(12) United States Patent
Orbay et al.

(10) Patent No.: US 8,506,606 B2
(45) Date of Patent: Aug. 13, 2013

(54) INTERNAL JOINT STABILIZER DEVICE, SYSTEM, AND METHOD OF USE

(75) Inventors: Jorge L. Orbay, Miami, FL (US); Thomas H. Norman, Miami, FL (US); Alex Espinosa, Miami, FL (US); William Garcia De Quevedo, Miami, FL (US); Juan Salcedo, Miami, FL (US)

(73) Assignee: Skeletal Dynamics, LLC, Miami, FL (US)

( * ) Notice: Subject to any disclaimer, the term of this patent is extended or adjusted under 35 U.S.C. 154(b) by 847 days.

(21) Appl. No.: 12/534,595

(22) Filed: Aug. 3, 2009

(65) Prior Publication Data

US 2010/0063549 A1    Mar. 11, 2010

Related U.S. Application Data

(60) Provisional application No. 61/085,651, filed on Aug. 1, 2008, provisional application No. 61/094,228, filed on Sep. 4, 2008, provisional application No. 61/100,138, filed on Sep. 25, 2008, provisional application No. 61/139,274, filed on Dec. 19, 2008, provisional application No. 61/163,693, filed on Mar. 26, 2009.

(51) Int. Cl.
*A61B 17/80* (2006.01)

(52) U.S. Cl.
USPC .......................................... 606/280; 606/286

(58) Field of Classification Search
USPC ................... 606/280, 286; 623/20.11–20.13
See application file for complete search history.

(56) References Cited

U.S. PATENT DOCUMENTS

| | | | |
|---|---|---|---|
| 4,242,758 A | 1/1981 | Amis et al. | |
| 5,571,103 A | 11/1996 | Bailey | |
| 5,891,144 A * | 4/1999 | Mata et al. | 606/59 |
| 6,162,223 A | 12/2000 | Orsak et al. | |
| 6,217,582 B1 | 4/2001 | Slocum | |
| 6,520,961 B1 | 2/2003 | Marsh | |
| 7,449,028 B2 * | 11/2008 | Ball | 623/20.13 |
| 2004/0260398 A1 * | 12/2004 | Kelman | 623/19.11 |
| 2009/0254189 A1 * | 10/2009 | Scheker | 623/21.11 |

OTHER PUBLICATIONS

International Search Report dated Mar. 24, 2010.

\* cited by examiner

*Primary Examiner* — Nicholas Woodall
(74) *Attorney, Agent, or Firm* — Laurence A. Greenberg; Werner H. Stemer; Ralph E. Locher

(57) ABSTRACT

A stabilization device is provided including an axle and a portion that can be affixed to a bone. The device is used to stabilize a joint while allowing motion of the joint along its natural trajectory and it is placed internally in order to prevent pin tract problems. Additionally, methods for using the device are provided that include, in various sequences, inserting the axle into a bone of a joint, adjusting the geometry of the device and attaching the fixable portion to another bone of the joint. The device can be provided as part of a system including an axis trajectory guide useful for locating the axis of rotation of the joint prior to insertion, adjustment and attachment of the device.

43 Claims, 27 Drawing Sheets

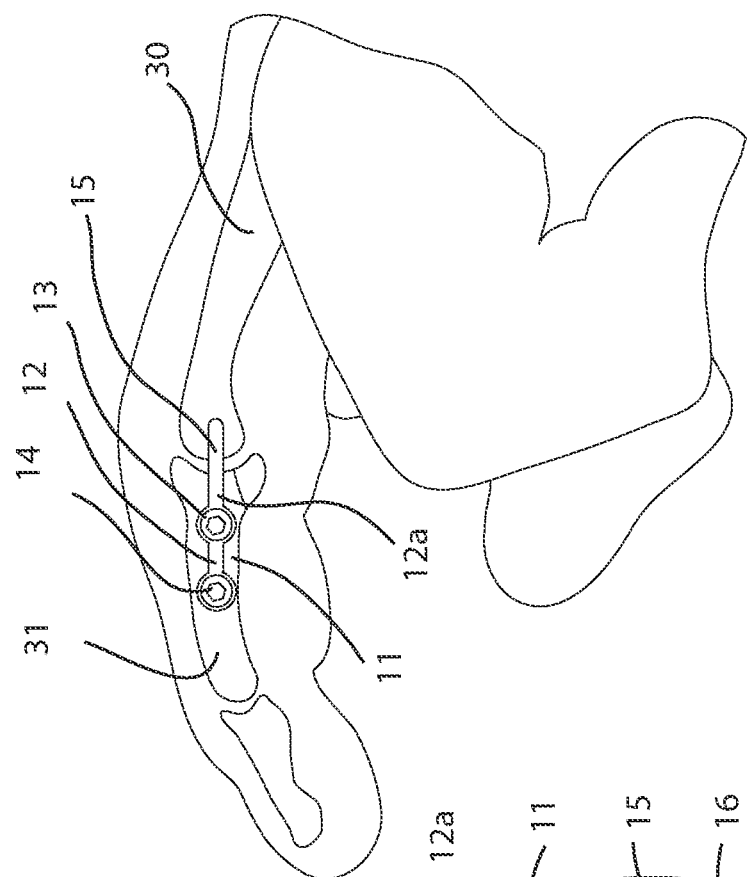
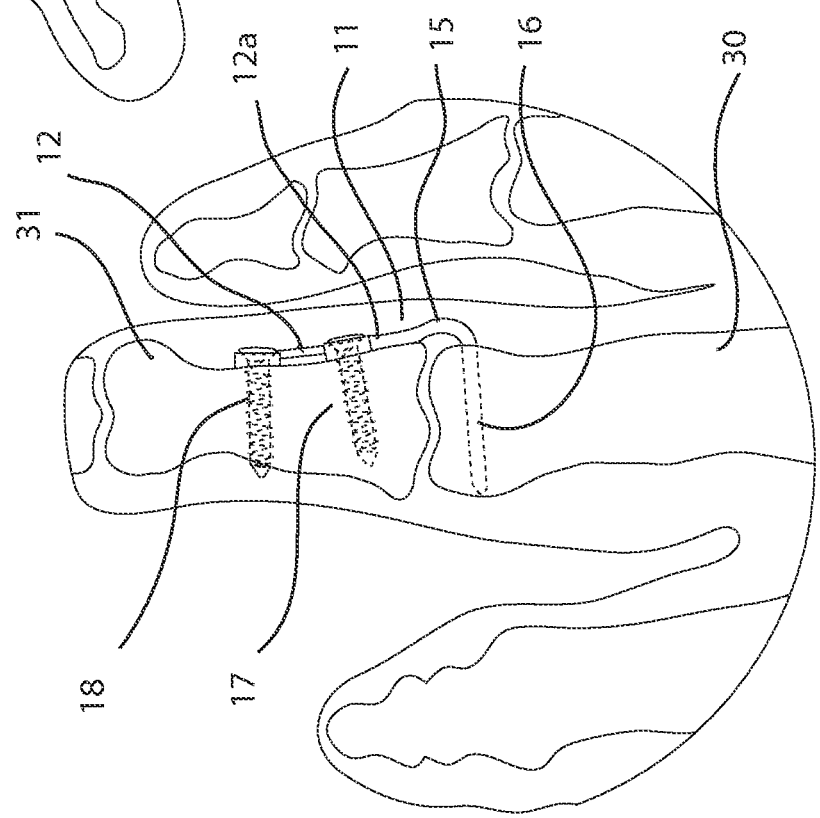
FIG. 5
FIG. 4

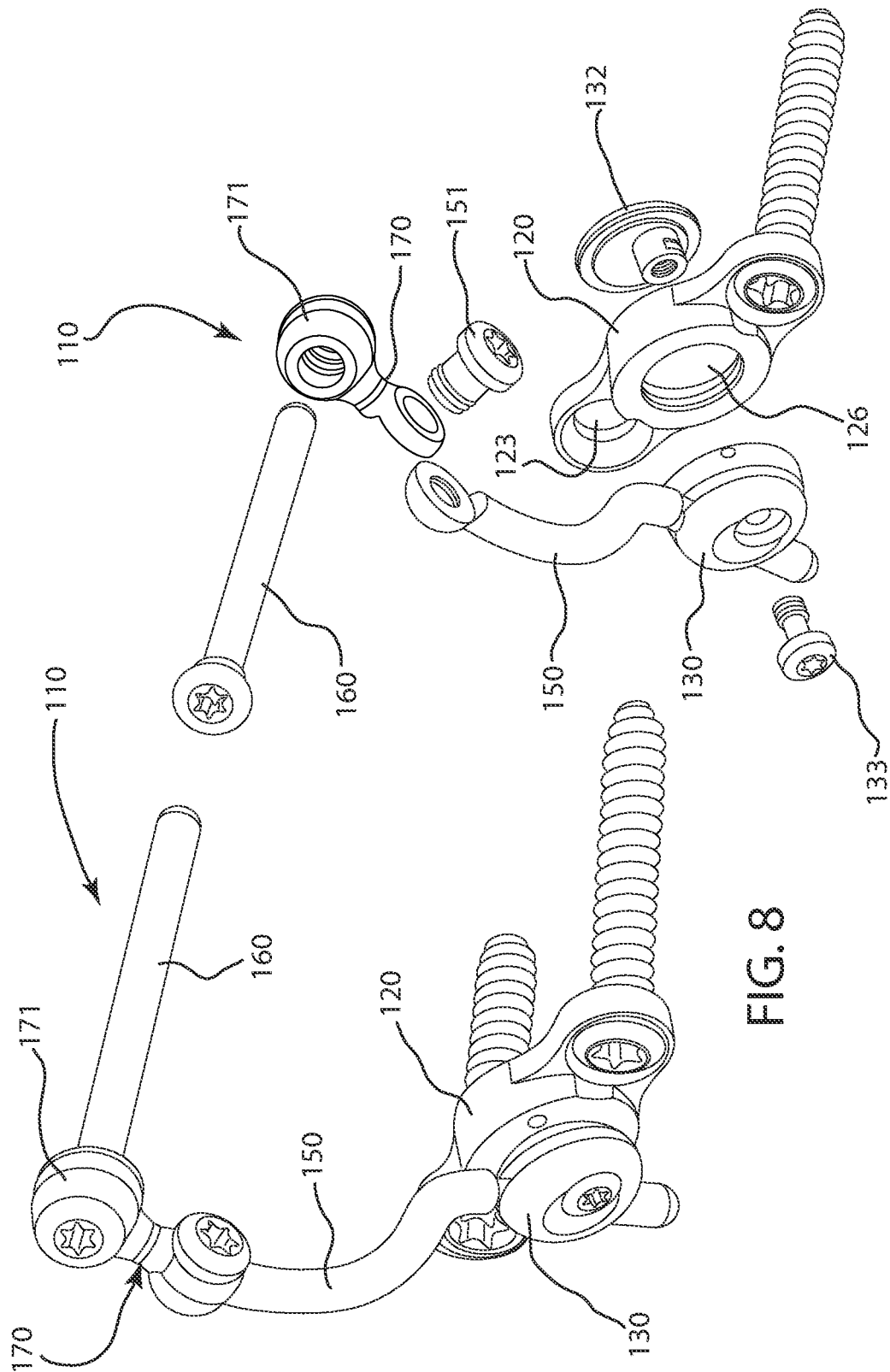

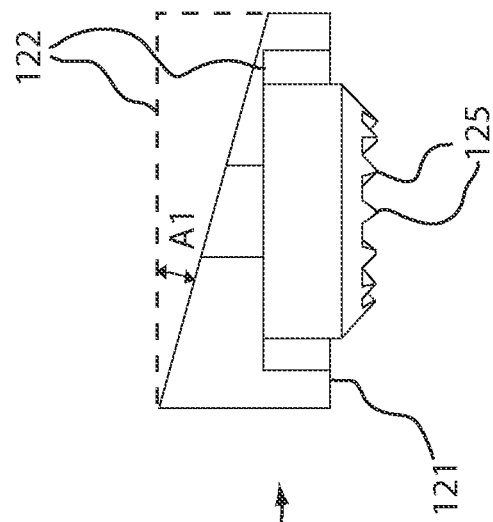
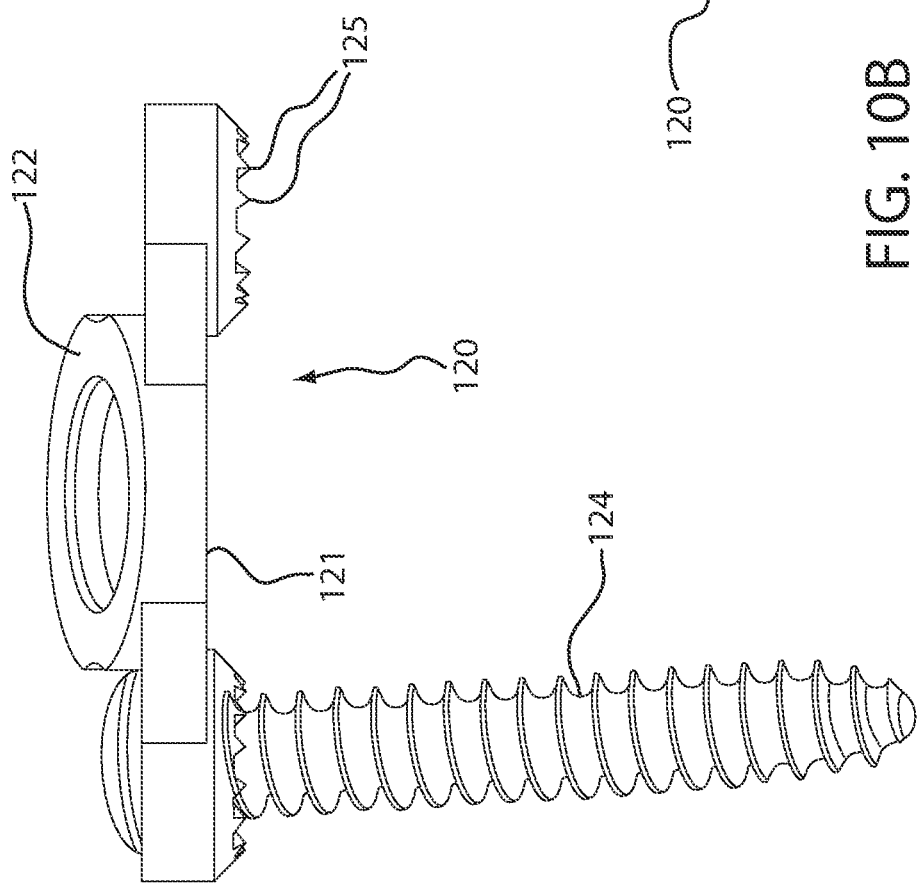

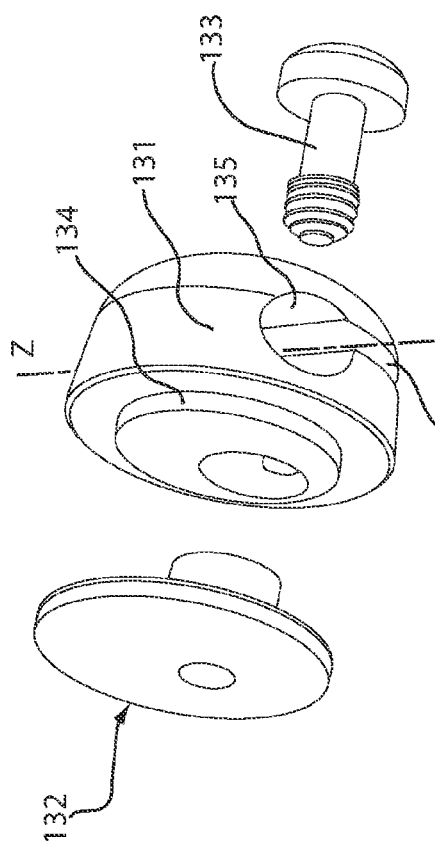
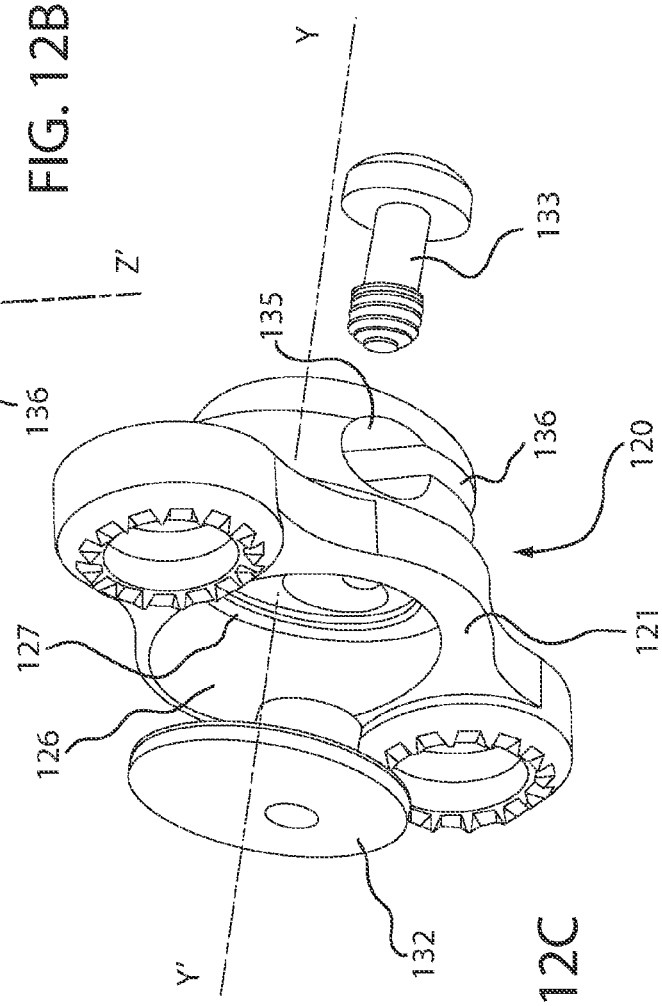
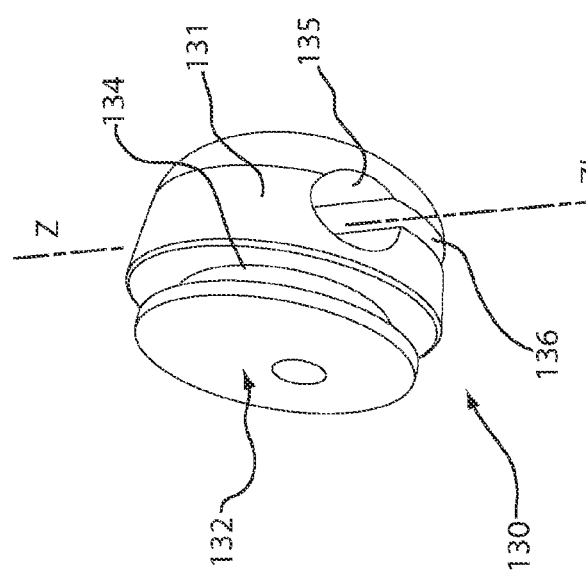

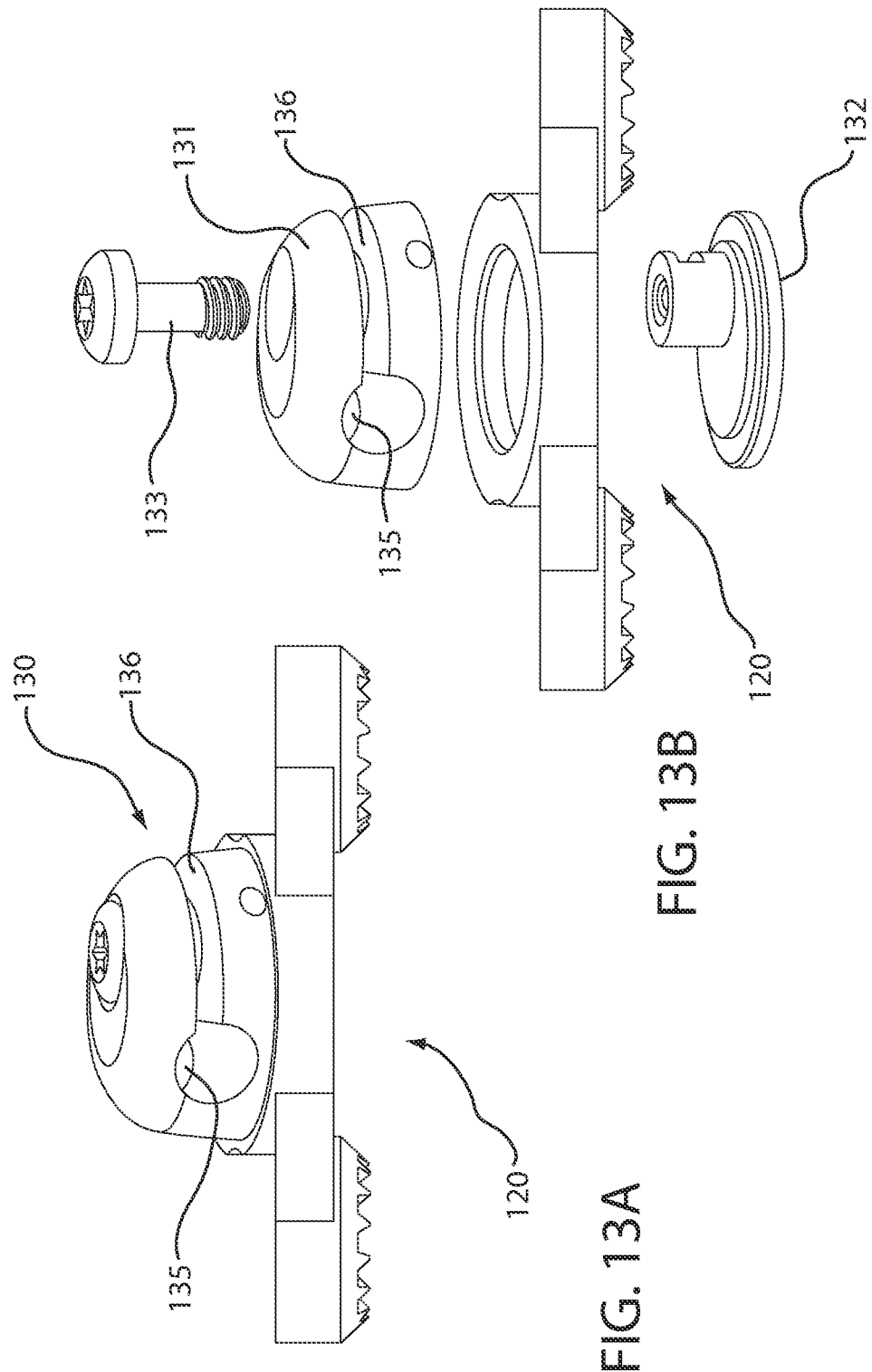

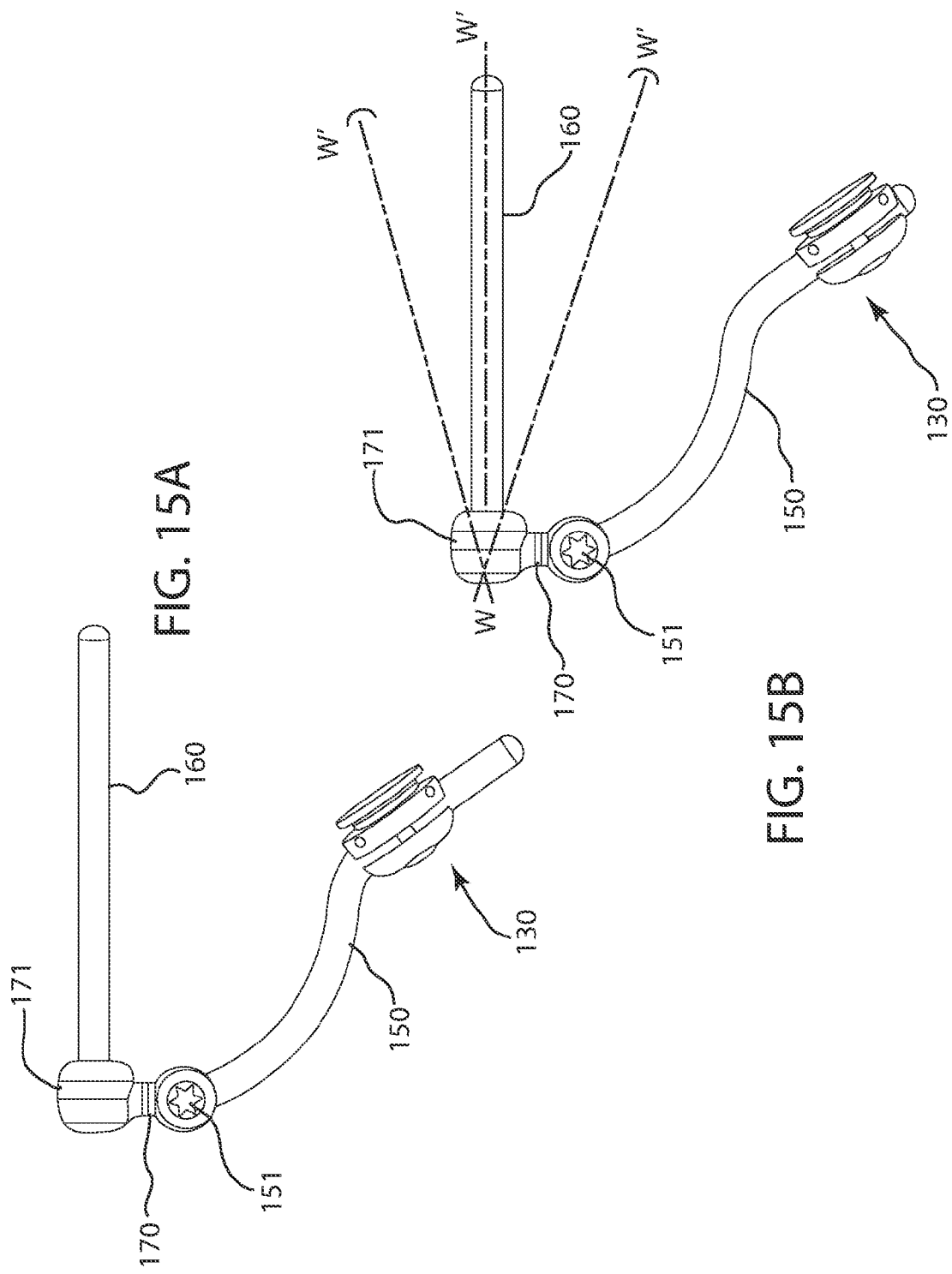

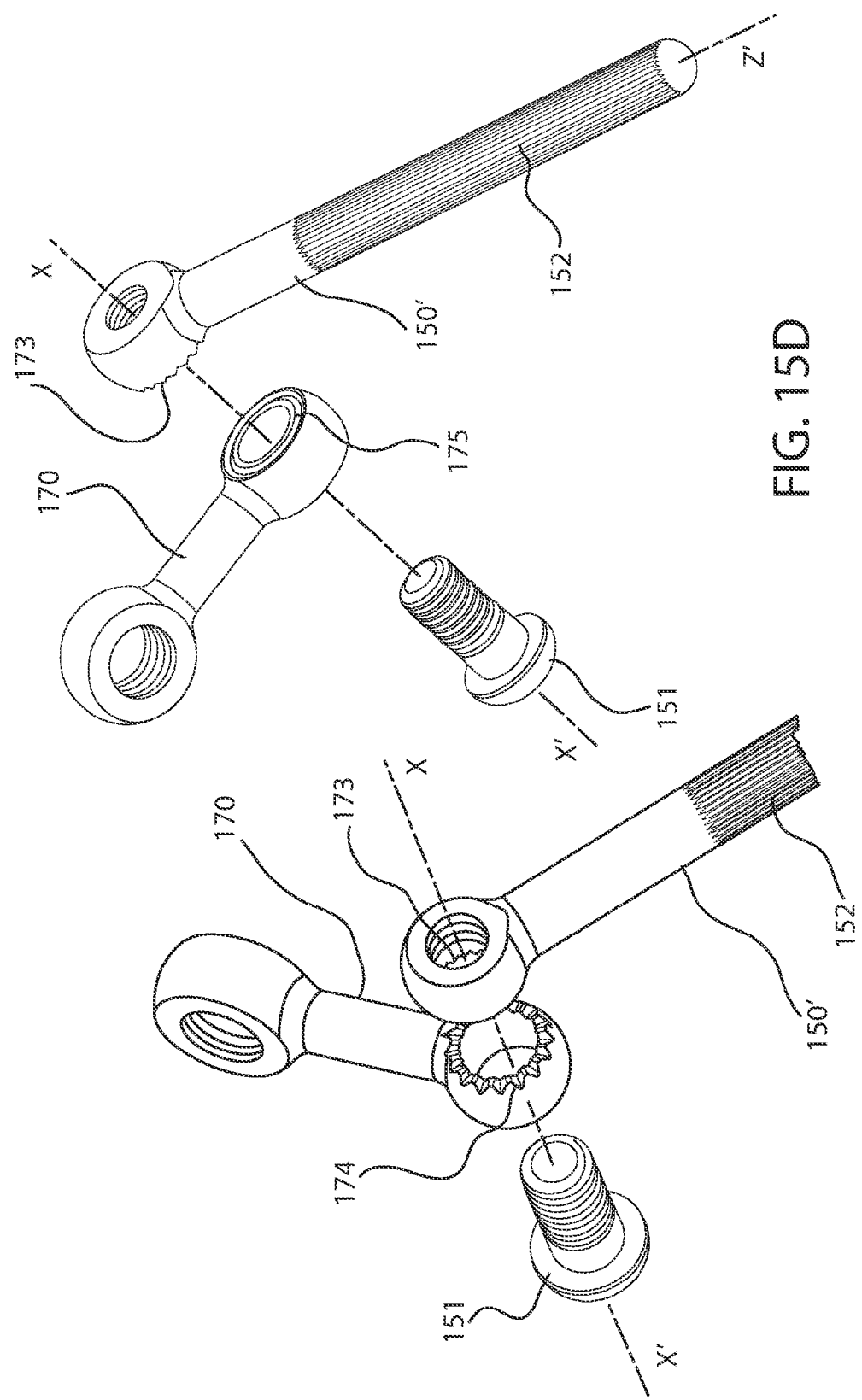

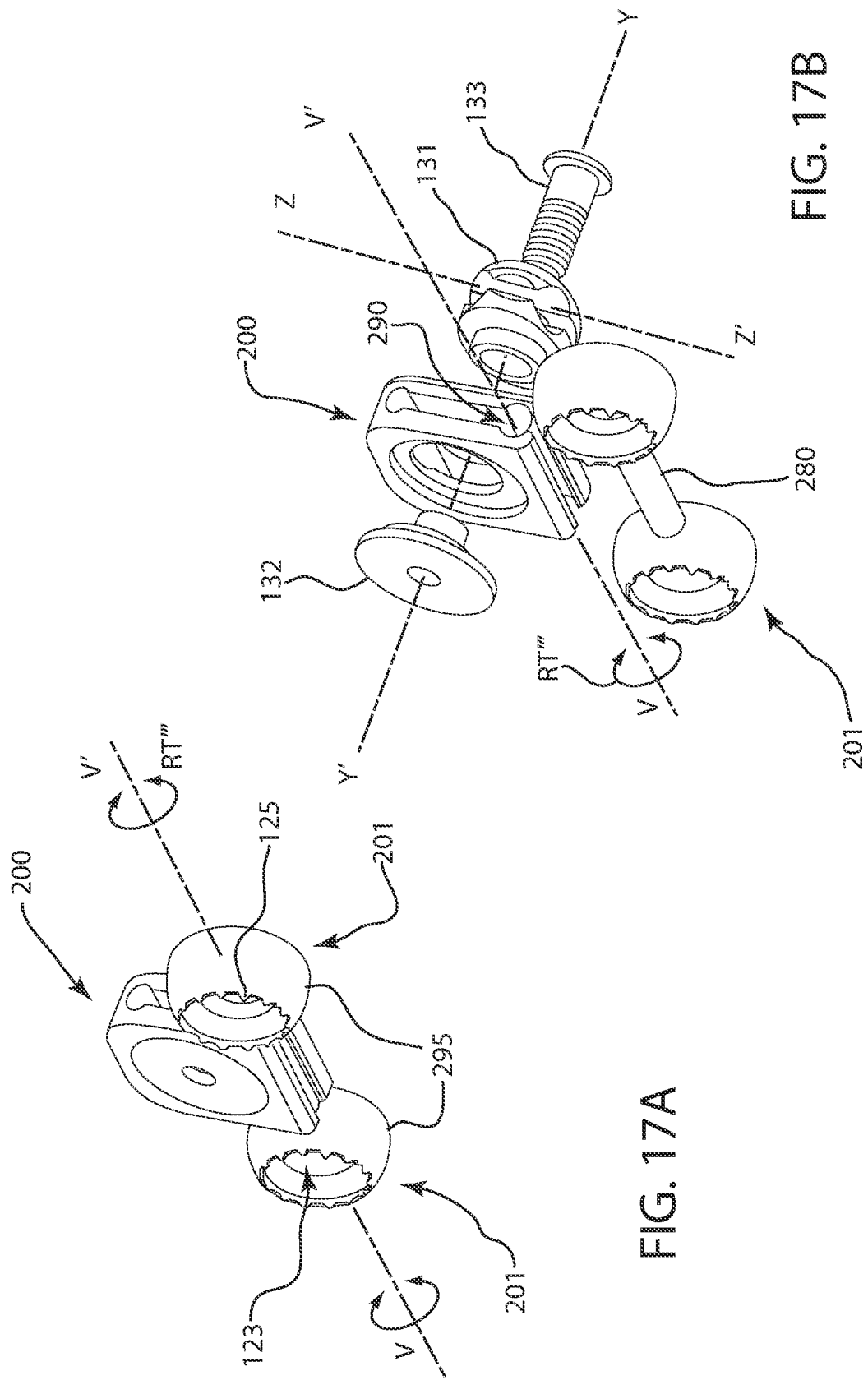

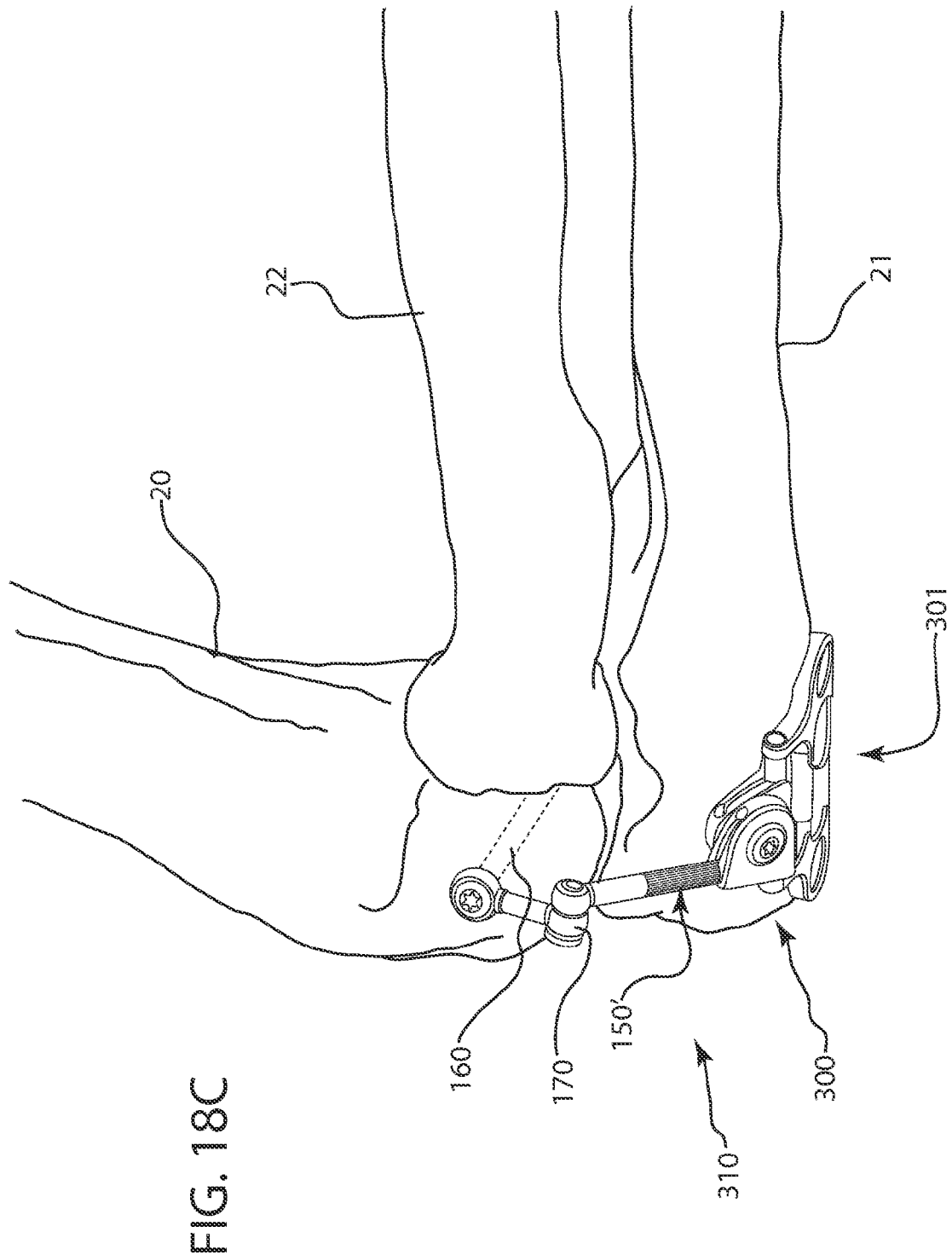

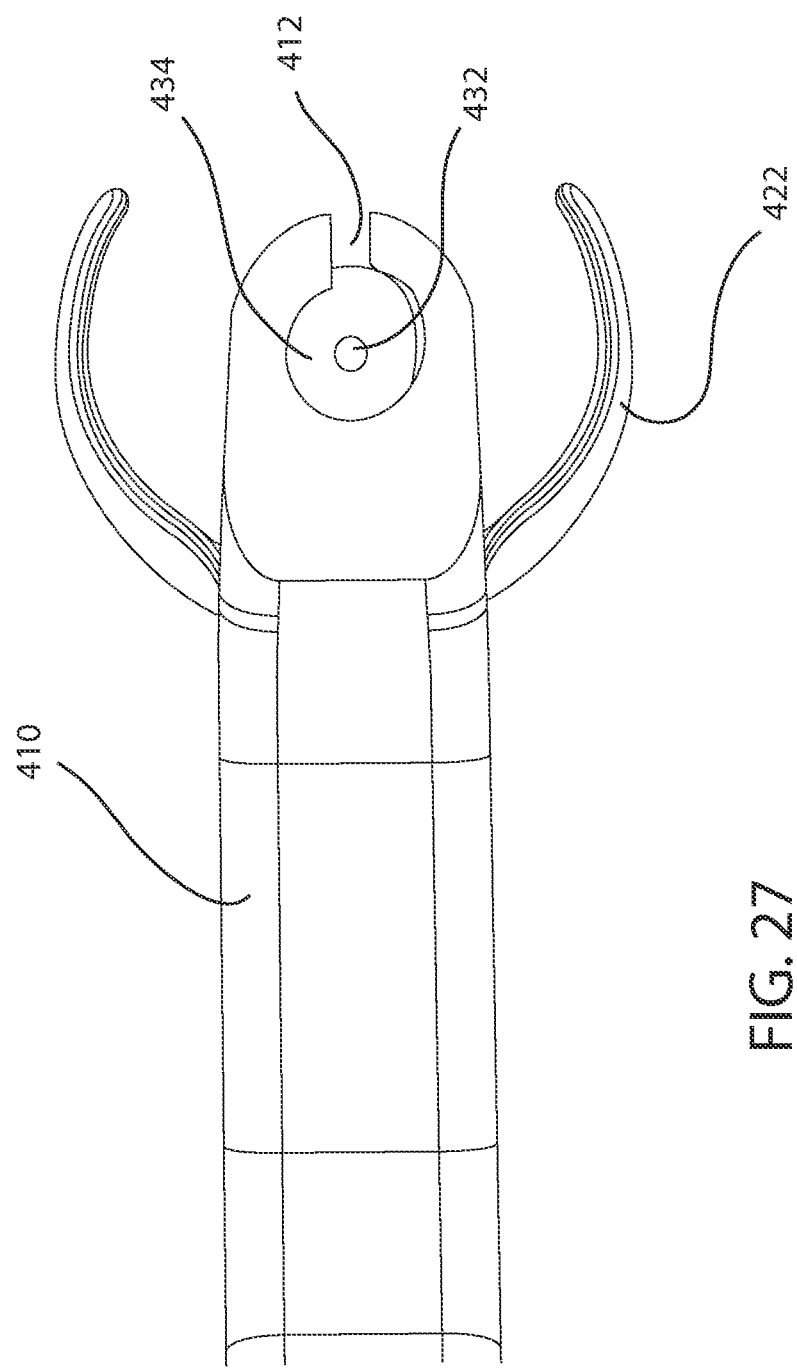

INTERNAL JOINT STABILIZER DEVICE, SYSTEM, AND METHOD OF USE

CROSS-REFERENCE TO RELATED APPLICATION

The present application claims priority to: Provisional Patent Application No. 61/085,651, filed on Aug. 1, 2008 and entitled "Internal Joint Stabilizer And Method Of Use"; Provisional Patent Application No. 61/094,228, filed on Sep. 4, 2008 and entitled "Internal Joint Stabilizer And Method Of Use"; Provisional Patent Application No. 61/100,138, filed on Sep. 25, 2008 and entitled "Internal Joint Stabilizer And Method Of Use"; and Provisional Patent Application No. 61/139,274, filed on Dec. 19, 2008 and entitled "Internal Joint Stabilizer And Method Of Use"; and Provisional Patent Application No. 61/163,693, filed on Mar. 26, 2009 and entitled "Axis Locator Jig And Method"; those applications being incorporated herein, by reference, in their entireties.

BACKGROUND OF THE INVENTION

The invention relates to the stabilization of joints for the purpose of facilitating healing and the early re-establishment of adequate range of motion at the joints.

DESCRIPTION OF THE RELATED ART

Dislocation and subluxation of joints are serious clinical problems that if persistent, recurrent or chronic can result in irreversible damage. These chronic instabilities are usually the result of damage to the supporting joint ligaments and/or the result of loss of bony integrity. Treatment of these conditions includes restoration of the proper relationships or "reduction" of the bones involved. Reduction must be maintained for a period of time sufficient to allow for healing of the damaged tissues. Also, it is desirable to maintain joint motion during this period in order to prevent ankylosis and to maintain a healthy articular cartilage. Thus, the ideal immobilization for a dislocated or subluxed joint would prevent abnormal translational movements but allow motion similar to its normal kinematics.

Hinged external fixators have been devised for the purpose of allowing the desired motion in the joint after reduction of the dislocation. These external fixators have been used primarily on the elbow but can also be used on the knee or the ankle. Hinged external fixators have provided satisfactory end results, allowing patients to regain adequate range of motion as well as stability of the joint. However, despite being considered "external" devices the installation of hinged external fixators require open surgery in order to properly identify the axis of rotation of the joint, a critical aspect of their functionality, because it has proven difficult or impossible to determine such axis from outside the body. Surgery, open or percutaneous, is also required to affix the position of the installed hinged external fixator by inserting multiple pins into the adjacent bones.

The intrinsic bulkiness of external fixators, combined with pain and frequent complications at the pin tracts have limited the quality of the clinical results of these devices. Patients have difficulty in actively moving these joints primarily due to pain in the pin tract sites. Patients are also limited in carrying out everyday functions due to the cumbersome nature of the device which must remain installed for a relatively long time, normally five or six weeks on average.

The need remains for a device that will maintain reduction while allowing early post-operative normal motion of the joint but that will eliminate the problems of device bulkiness and pin tract pain and complications associated with existing hinged external fixators.

There additionally exists a need for a guide, system and method for locating the axis of rotation of a joint, prior to stabilization and for, subsequently, affixing a joint stabilizer.

BRIEF SUMMARY OF THE INVENTION

It is accordingly an object of this invention to provide an internal joint stabilizer device, system and method which overcomes the above-mentioned disadvantages of the heretofore-known devices. A joint stabilizer device is provided including an axle and a portion that can be affixed to a bone. The device is placed internally in order to prevent pin tract problems and to stabilize the joint while allowing motion of the joint along its natural trajectory.

Additionally, a method for using the device is provided that includes inserting the axle into a first bone forming a joint, and attaching the fixable portion to a second bone of the joint. A trajectory guide that can optionally be used to locate the axis of rotation of the joint, prior to stabilization, is additionally provided.

Although the invention is illustrated and described herein as embodied in an Internal Joint Stabilizer Device, System and Method, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 4 is a plan view of the internal joint stabilizer after it has been installed in an interphalangeal joint.

FIG. 5 is a side elevational view of the internal joint stabilizer of FIG. 4 after it has been installed in an interphalangeal joint.

FIG. 8 is a perspective view of a further particular embodiment of the internal joint stabilizer of the instant invention.

FIG. 9 is an exploded perspective view of the internal joint stabilizer of FIG. 8.

FIGS. 10A and 10B are enlarged side elevation views of the plate portion of the internal joint stabilizer of FIG. 8.

FIGS. 12A, 12B, 12C, 13A and 13B are enlarged perspective views of the turret portions of the internal joint stabilizer of FIG. 8.

FIGS. 15A-15B are side elevational views, and FIGS. 15C-15D are exploded perspective views, of selected portions of the internal joint stabilizer of FIG. 14.

FIGS. 17A and 17B are perspective and exploded perspective views of a further embodiment of the plate portion and turret assembly of the internal joint stabilizer of FIG. 8.

FIG. 18C is a perspective view an internal joint stabilizer using the selected portions shown in FIGS. 18A-18B.

FIGS. 21-27 illustrate one particular method of using the axis trajectory guide of FIG. 19.

DETAILED DESCRIPTION OF THE INVENTION

Figure 1:
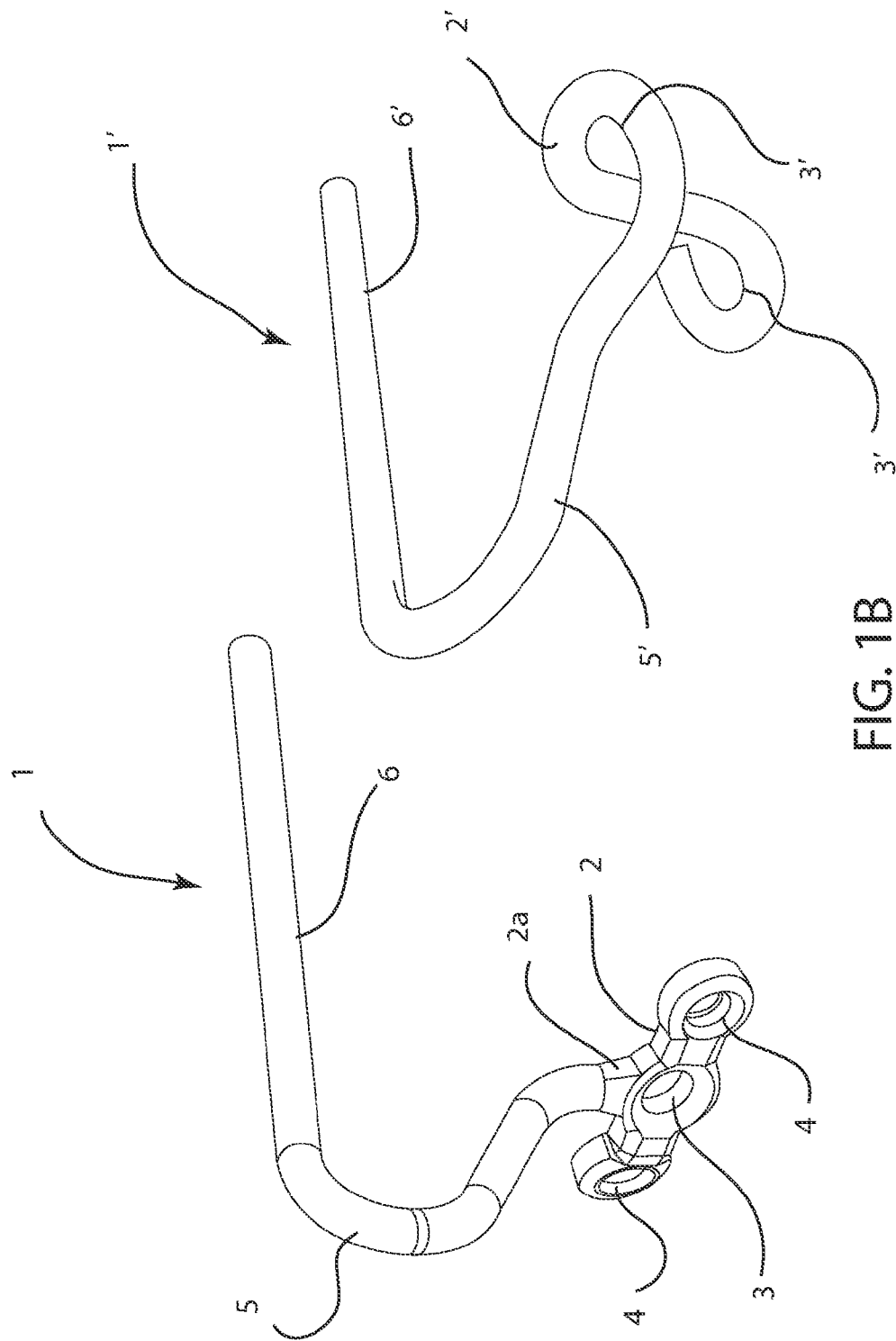
FIGS. 1A and 1B are perspective views of two different particular embodiments of an internal joint stabilizer of the instant invention.
Figure 2:
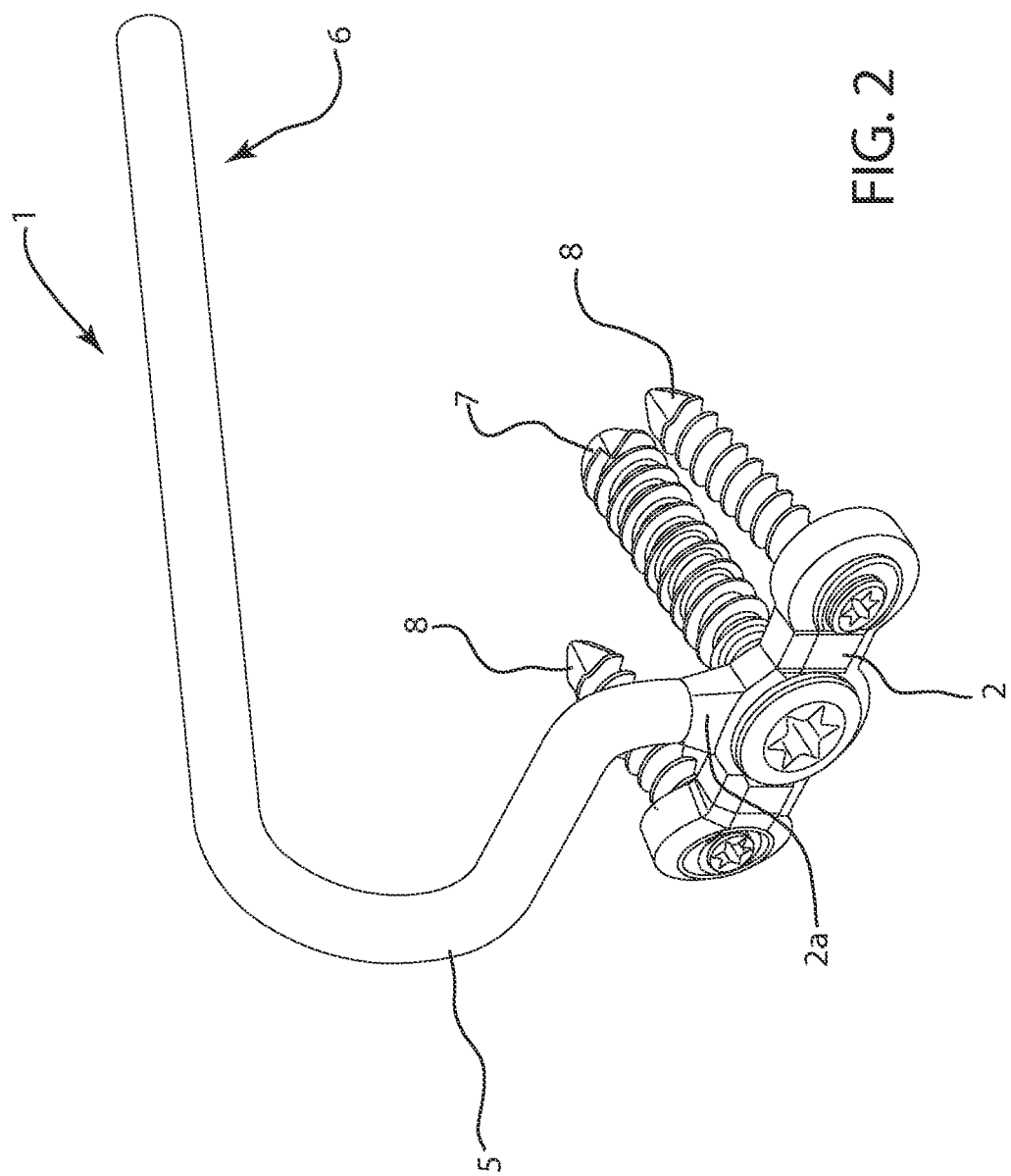
FIG. 2 is a perspective view of the internal joint stabilizer of FIG. 1A with bone screws attached.

Referring now to the figures of the drawings in detail and, more particularly, to FIGS. 1A and 2, there is shown one particular embodiment of an internal joint stabilizer 1 in accordance with the present invention. The internal joint stabilizer 1 is designed to be placed internally, so as to prevent pin tract problems and to stabilize the joint, while allowing motion at the joint along its natural trajectory.

The internal joint stabilizer 1 of FIG. 1A, is particularly adapted for use in connection with hinged joints, such as an elbow, and is preferably made of metal (such as titanium, cobalt chrome or stainless steel or a combination of titanium portions and cobalt chrome portions); bioabsorbable material (such as PLA or PGA) or a combination of metal and bioabsorbable material. The internal joint stabilizer 1 includes a plate portion 2, which is, preferably, formable (i.e., bendable). Extending through the plate portion 2 are holes 3 and 4, which are adapted to receive bone screws 7 and 8. Note that the holes 3 and/or 4 can be embodied by a slot and that none, more or fewer holes 3 and/or 4 to receive bone screws 7, 8 can be included in the plate portion 2, as desired. The bone screw 7 is preferably a compression screw to be attached to a bone through hole or slot 3. If provided, holes 4 are preferably adapted to receive, indiscriminately, compression screws and/or angle-stable screws 8 to be attached to the same bone as screw 7, at an angle selected by the surgeon. If selected, angle-stable screws 8 become engaged with holes 4 upon fully setting, providing further stability at the selected angle. Note that, as shown more particularly in FIG. 1B, an internal joint stabilizer in accordance with the instant invention can have a very simple form. For example, the entire internal joint stabilizer 1' of FIG. 1B, including the fixable portion 2', holes 3', neck portion 5' and axle portion 6' can be made from a section of K-wire or a Steinmann pin, for example, partially pre-bent to form, at least, holes 3' configured to receive compression and/or angle stable screws and still be within the scope of the instant invention.

Referring now to FIGS. 4 and 5, there is shown another particular embodiment of an internal joint stabilizer 11 in accordance with the present invention. The internal joint stabilizer 11 is designed to be placed internally, so as to prevent pin tract problems and to stabilize the joint, while allowing motion at the joint along its natural trajectory.

The internal joint stabilizer 11 of FIGS. 4, 5 is particularly adapted for use in connection with other hinged joints, such as the interphalangeal joints of the hand known as PIP (proximal interphalangeal joint), DIP (distal interphalangeal joint) and IP (interphalangeal joint of the thumb), and is preferably made of metal (such as titanium, cobalt chrome or stainless steel), bioabsorbable material or a combination of both. The internal joint stabilizer 11 includes a plate portion 12 which is preferably formable. Extending through the plate portion 12 are hole or slot 13 and holes 14, which are adapted to receive bone screws 17 and 18. Note that none, fewer or more holes 14 to receive bone screws 18 can be included in the plate portion 12, as desired. The bone screw 17 is preferably a compression screw to be attached to a bone through hole or slot 13. If provided, holes 14 are preferably adapted to receive, indiscriminately, compression and/or angle-stable screws 18 to be attached to the same bone as screw 17, at an angle selected by the surgeon. If selected, angle-stable screws 18 become engaged with holes 14, upon fully setting, providing further stability at the selected angle.

Referring now to FIGS. 1A, 2, 4 and 5 the internal joint stabilizer 1, 11 additionally includes a neck portion 5, 15 extending from the edge 2a, 12a of the plate portion 2, 12. An axle portion 6, 16 extends from the end of the neck portion 5, 15 distal from the plate 2, 12. The neck portion 5, 15 is preferably formable (i.e., bendable) such that it can be formed by the surgeon intraoperatively in any of three axes X, Y, Z to conform to the anatomy of the patient after the axle portion 6, 16 has been placed in alignment with the natural axis of rotation of the hinged joint where it is being used. As an example, in the case where the hinged joint is the elbow, the plate portion 2 would be rigidly affixed to the ulna on its lateral, posterior or its medial aspect, while the axle portion or projection 6 would project through a hole in the humerus, aligned to the natural axis of joint rotation. In another example, in the case where the hinged joint is an interphalangeal joint, the plate portion 12 would be rigidly affixed to the more distal phalanx on its ulnar or radial aspect, while the axle portion or projection 16 would project through a hole in the more proximal phalanx, aligned to the natural axis of joint rotation. It should be noted that the relationship between the plate portions 2, 12 and neck portions 5, 15 of internal joint stabilizers 1, 11 have been adapted to the anatomy to which the internal joint stabilizer is being applied. In the case of internal joint stabilizer 1 the axis of the neck portion tends to be substantially perpendicular to the axis of the plate portion (i.e. forming an inverted T) while in the case of internal joint stabilizer 11 the axis of the neck portion tends to be substantially in line with the axis of the plate portion. The relationship between the plate portion and the neck portion can be further adapted for other parts of the anatomy where the internal joint stabilizer will be applied while staying within the scope of the present invention.

The plate portion 2, 12 and neck portion 5, 15, respectively, of the internal joint stabilizer 1, 11 could be constructed in accordance with that described in U.S. patent application Ser. No. 12/463,037, which application is being incorporated herein, by reference, in its entirety.

Figures 3, 3A:
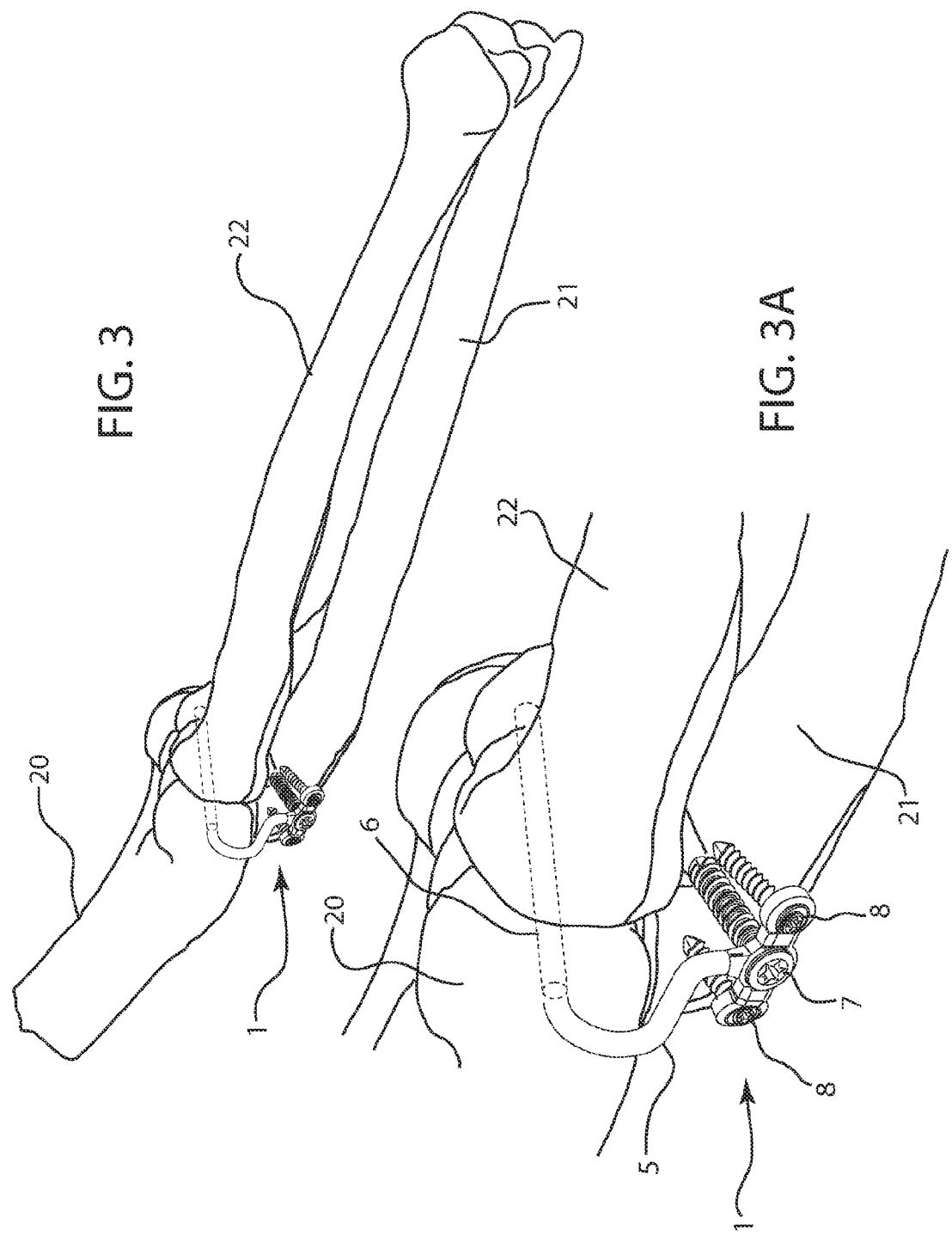
FIG. 3 is a perspective view of the internal joint stabilizer of FIG. 2 after it has been installed in the humero-ulnar joint.
FIG. 3A is an enlarged detail view of the humero-ulnar joint of FIG. 3.

One particular method of utilizing the internal joint stabilizer 1 will now be described in connection with FIGS. 1A-3A. More particularly, FIGS. 3-3A illustrate the internal joint stabilizer 1 attached to the humero-ulnar joint. It can be seen that the axle portion 6 (shown in dotted line) has been inserted into the humerus 20, in alignment with the natural axis of rotation of the humero-ulnar joint. The plate portion 2 is attached to the ulna 21 (in this example, on the lateral side) using the bone screw 7, in compression mode, while the screws 8 further attach the plate portion 2 to the ulna 21 in compression or in angle-stable mode. Additionally, the radius bone 22 is shown for reference only, since it is not affected by the procedure.

Furthermore, FIGS. 4 and 5 illustrates the internal joint stabilizer 11 attached to an interphalangeal joint (a PIP joint, in particular). It can be seen that the axle portion 16 (shown in dotted line) has been inserted into the more proximal phalanx 30, in alignment with the natural axis of rotation of the interphalangeal joint. The plate portion 12 is attached to the ulnar (shown) or the radial aspect of the more distal phalanx 31 using the bone screw 17, in compression mode, while the screws 18 further attach the plate portion 12 to the more distal phalanx 31 in compression or in angle-stable mode.

To install the internal joint stabilizer the surgeon approaches the affected joint through lateral and/or medial incisions (in the case of the elbow) or radial and/or ulnar incisions (in the case of the interphalangeal joint). The dislocated joint is reduced and a first point on the axis of rotation of the joint determined. This can be accomplished by visual inspection of the anatomy. Alternatively, the joint can be moved through its range of motion allowing the surgeon to identify and mark the isometric point on the proximal bone of the joint (the humerus in the case of the elbow or the more proximal phalanx of the affected joint in the case of an interphalangeal joint) which locates a first point on the axis of rotation. In the case of the elbow this point is located in the center of the capitellum next to the base of the lateral epicondyle. Similarly, a second point on the axis of rotation on the opposite side of the proximal bone 20, 30 of the joint can be identified by fluoroscopy, direct inspection or with the aid of a specialized axis trajectory guide (for example, the axis trajectory guide 400 of FIG. 19) and marked. A hole is then drilled through the axis of rotation in preparation for installation of the internal joint stabilizer.

The axle portion 6, 16 is then inserted in the hole drilled in the proximal bone of the joint. If and as required, the neck portion of the internal joint stabilizer is then formed by the surgeon in such a way that hole or slot 3, 13 of the plate portion 2, 12 will lie in its proper position, flat against the relatively flat portion of the lateral (shown), posterior or medial aspect of the ulna 21 in the case of the elbow or the radial or ulnar (shown) aspect of the more distal bone of the affected joint 31 in the case of an interphalangeal joint. A bone screw 7, 17 is inserted into hole or slot 3, 13 and screwed into the bone. If holes or slots 4, 14 are provided, the plate portion 2, 12 is further formed by the surgeon, as required, so that holes or slots 4, 14 lie approximately flat against the lateral (shown), posterior or medial aspect of the ulna 21 in the case of the elbow or the radial or ulnar (shown) aspect of the more distal bone of the affected interphalangeal joint. Compression or angle-stable screws 8, 18 are then inserted into holes 4, 14 at an angle selected by the surgeon and screwed into the ulna 21 or phalanx 31 as the case may be. If desired, after screws 8, 18 have been attached, the bone screws 7, 17 that were originally affixed through holes or slots 3, 13 may be removed and substituted by angle-stable screws 8, 18.

Range of motion and stability of the joint is again tested. Incisions are closed by the surgeon in standard fashion.

If required, internal joint stabilizers made of metal may be removed surgically after a period of time sufficient to allow healing of the damaged tissues. In an alternate embodiment all or some portions of the stabilizer or, at least, its axle portion would be made of bioabsorbable material, i.e.: polylactic acid, thus reducing the need for surgical removal of some or all portions of the internal joint stabilizer.

Figure 6:
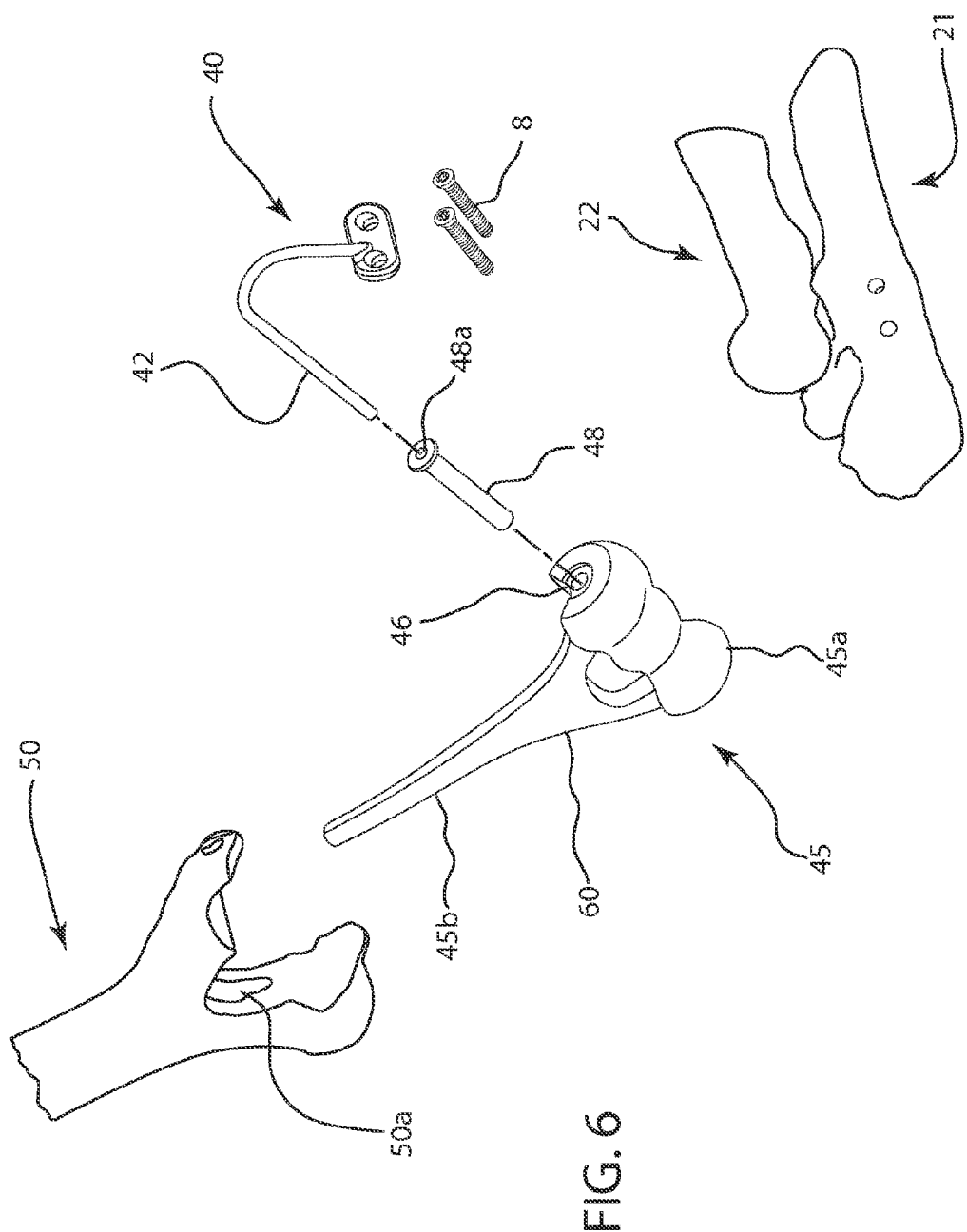
FIG. 6 is an exploded perspective view of an exemplary joint including an internal joint stabilizer of the instant invention used in conjunction with a prosthetic implant, in accordance with a further embodiment.
Figure 7:
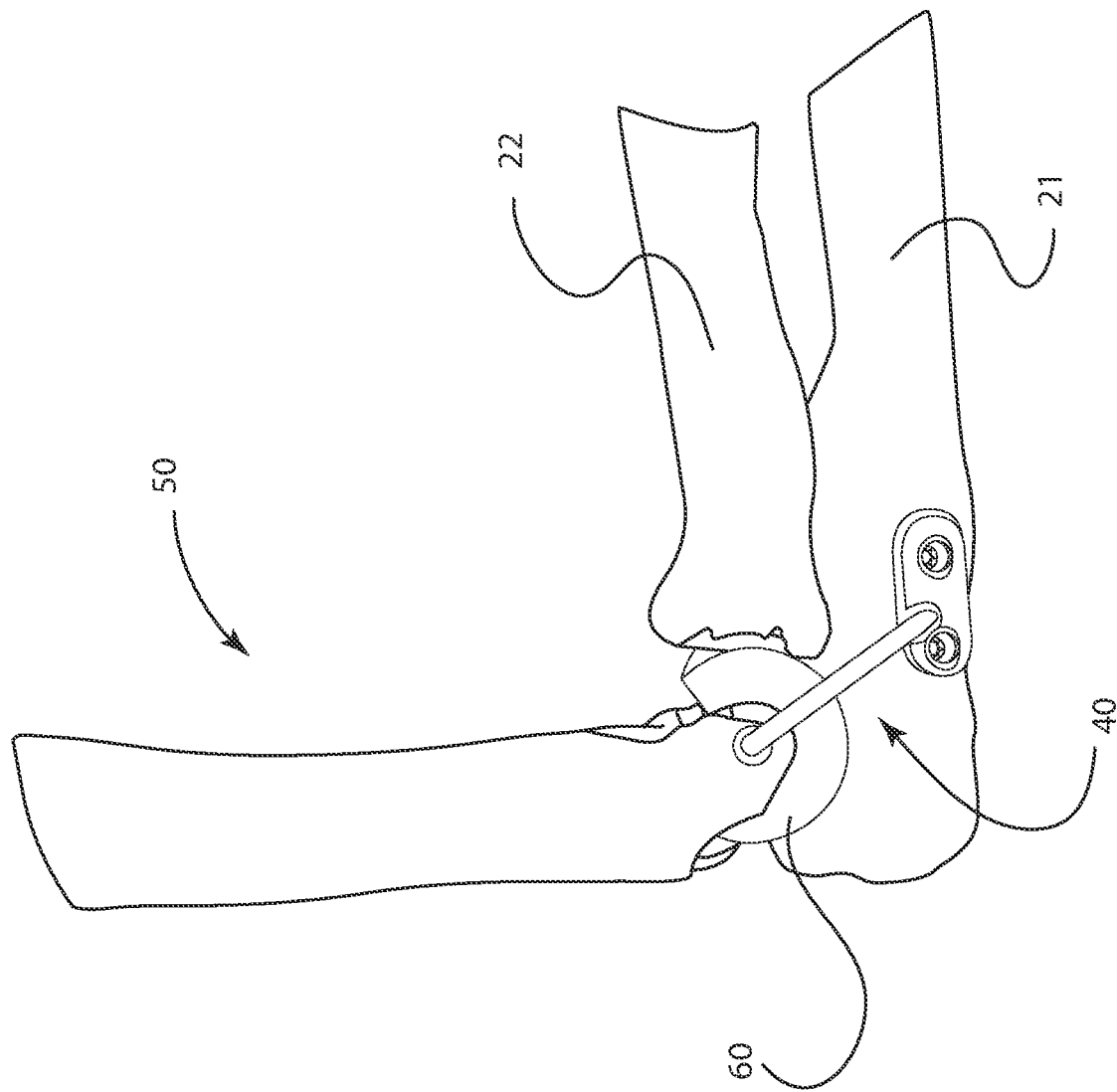
FIG. 7 is a side elevational view of an exemplary joint including the internal joint stabilizer of FIG. 6 after installation.

Referring now to FIGS. 6 and 7, there is shown a further embodiment of an internal joint stabilizer 40 in accordance with the instant invention. In certain cases, the surface or end of the proximal bone 50 of the joint may be damaged, and may need to be replaced. As such, in accordance with the principles of the present invention, an axle portion 42 of the internal joint stabilizer 40 of the present invention can be inserted into a prosthetic implant 60 inserted into the damaged proximal bone 50. For example, as shown in FIGS. 6 and 7, the internal joint stabilizer 40 is particularly adapted for use in the cases where the articular surface of the proximal bone 50 (in this case, the humerus of the humero-ulnar joint) is damaged and needs to be replaced by a prosthetic implant 45. Note that the exemplary use of the humero-ulnar joint is not meant to be limiting, as the use of the internal joint stabilizer 40 can be adapted for use in other joints (for example, in the PIP joint) when the use of a prosthetic implant is indicated.

As shown more particularly in FIG. 6, in the present example, a prosthetic implant 45 is provided that includes a surface 45a to replace the damaged articular surface of the humerus 50 and a shaft 45b to be inserted into, and affixed to, the medullary cavity 50a of the humerus 50. The prosthetic implant also includes a pre-drilled hole 46 sized to receive the axle portion 42 of the internal joint stabilizer 40. Alternatively, the surgeon may drill the hole 46 for the axle 42 intra-operatively. Optionally, a bearing sleeve 48 preferably made of plastic material can be provided to be inserted into the hole 46 of the prosthetic implant prior to inserting the axle 42 of the internal joint stabilizer 40. When using the optional bearing sleeve, the hole 46 in the prosthetic implant 45 will be sized and otherwise configured to receive the bearing sleeve 48.

To install the internal joint stabilizer shown in FIGS. 6 and 7, the surgeon approaches the affected joint (i.e., the elbow in the illustrated example) through an incision and proceeds to remove the damaged articular surfaces of the proximal bone 50 (for example, the humerus) as shown in FIG. 6, to prepare the medullary cavity 50a of the proximal bone 50 to receive the shaft 45b of the prosthetic implant 45. The prosthetic implant 45 is then inserted and affixed with screws and/or cement and/or other means to the proximal bone 50, such that the axis of the hole 46 is aligned with the natural axis of rotation of the proximal bone 50.

The axle portion 42 is then inserted into the hole 46 in the prosthetic implant 45. Alternately, if provided, the optional bearing sleeve 48 may be inserted into an appropriately sized hole 46 in the prosthetic implant 45 prior to inserting the axle portion 42 through a hole 48a into the bearing sleeve 48.

Once the axle portion 42 and/or bearing sleeve 48 and axle portion 42 has been inserted into the hole 46 in the prosthetic implant 45, the surgeon proceeds with the operation by following the steps previously described above in connection with the internal joint stabilizers of FIGS. 1-5.

Referring now to FIGS. 8-11B, there is shown another embodiment of an internal joint stabilizer 110 in accordance with the instant invention. The internal joint stabilizer 110 includes additional components directed towards providing additional degrees of adjustability. The present particular embodiment of the internal joint stabilizer 110 includes a plate portion 120, a turret assembly 130, a neck portion 150, a swivel joint 170, an eyelet 171 and an axle portion 160. All component portions of the internal joint stabilizer 110 but, at least, neck portion 150 and axle portion 160 can be provided in different sizes to accommodate the particular anatomy of the patient.

In particular, the internal joint stabilizer 110 includes a plate portion 120 which, in the preferred embodiment, is bendable (i.e., formable) intraoperatively. The plate portion defines an interior surface 121, configured to engage a bone, and an exterior surface 122, opposite the interior surface 121. As shown more particularly in FIG. 10B, the plane of the exterior surface 122 is preferably chosen to be oblique to the plane of the interior surface 121, diverging from parallel by an angle A1 in the range of 0>A1>=45 degrees. However, if desired, another angle can be chosen or the surface 122 may be selected to be parallel to the surface 121.

Figures 11A, 11B:
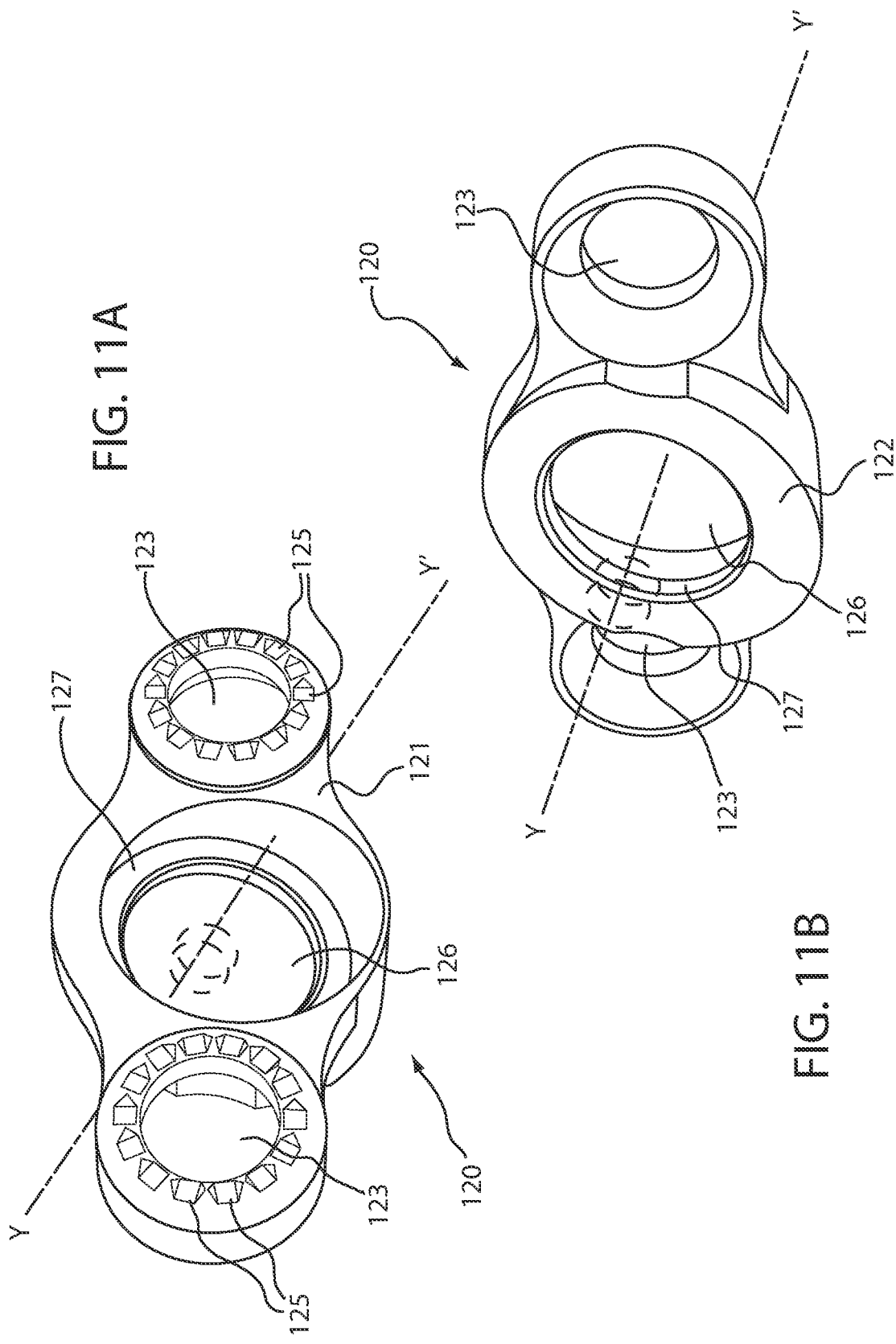
FIGS. 11A and 11B are enlarged perspective views of the plate portion of the internal joint stabilizer of FIG. 8.

As can be seen more particularly from FIGS. 11A and 11B, at least two holes 123 extend through the plate 120, between the interior surface 121 and the exterior surface 122. Holes 123 are adapted to receive a fixation device therethrough, for example, compression bone screws (124 of FIG. 10A) or angle-stable bone screws (not shown). In one particular embodiment, the perimeter surrounding the screw holes 123 on the interior surface 121 of the plate can be provided with protrusions 125 that enhance frictional engagement with the bone. Additionally, a turret hole 126 extends through the plate 120, between the interior surface 121 and exterior surface 122. Turret hole 126 includes a circumferential lip 127 and is adapted to receive a turret assembly (130 of FIG. 9). As shown in FIGS. 11A and 11B the turret hole 126 defines an axis Y-Y', perpendicular to exterior surface 122, around which the turret assembly (130) can rotate.

Referring now to FIGS. 11A to 14B, there will be described a turret assembly 130 for use with one particular embodiment of the present invention. Turret assembly 130 includes a turret portion 131, a turret nut portion 132 and a turret set screw 133. The turret portion 131 is dimensioned to be inserted into the turret hole 126 of the plate 120, from the side of the exterior surface 122, until it is engaged with (i.e., seated against the exterior wall of) the circumferential lip 127. The turret nut portion 132 is dimensioned to be inserted into the turret hole 126 from the side of the interior surface 121 of the plate 120 until it is seated against the interior surface of the circumferential lip 127. The turret portion 131 and the turret nut portion 132 are precisely dimensioned to fit inside their respective sides of the turret hole 126 while allowing sufficient clearance to permit their rotation inside the turret hole 126 around the axis Y-Y' (RT' of FIG. 14). The turret portion 131 and turret nut portion 132 are fixed loosely together, each on its respective side of the circumferential lip 127, by the turret set screw 133, with the lip portion 134 of the turret portion 131 disposed therebetween. The lip portion 134 of the turret assembly 130 is designed to loosely engage the circumferential lip 127 and permit rotation of the turret assembly 130. Further tightening of the turret set screw 133 draws the turret nut portion 132 into frictional engagement with the circumferential lip 127, thereby impeding further rotation of the turret assembly 130.

Referring now to FIGS. 12A-14, it can be seen that the turret portion 131 is provided with a hole 135, dimensioned to receive and frictionally engage with a neck portion 150. Hole 135 is preferably cylindrical with its centerline defining an axis Z-Z'. As additionally shown, in the present embodiment, the turret portion 131 also includes a slot 136 to facilitate clamping of neck portion 150 to turret portion 131 upon tightening of turret set screw 133. The slot 136 is parallel to the axis Z-Z' and extends through a portion of the turret portion 131, from one end of the hole 135 to the other end of the hole 135. Correspondingly, the neck portion 150 has a cylindrical cross-section and is dimensioned to be inserted, at least partially, into the cylindrical hole 135. Once inserted, neck portion 150 can rotate about the axis Z-Z' (RT of FIG. 14) within the cylindrical hole 135. Neck portion 150 can also slideably translate longitudinally along axis Z-Z' of hole 135 (TR of FIG. 14). However, once turret screw 133 is fully tightened into the turret nut portion 132, friction between hole 135 and neck portion 150 clamps neck portion 150 and impedes any further rotational or translational movement of the neck portion 150 within the hole 135. The mechanism for clamping the neck portion 150 described above is not intended to be limited to the details shown since other methods of clamping can be used without departing from the spirit of the invention and within the scope and range of equivalents of the claims.

Figure 14:
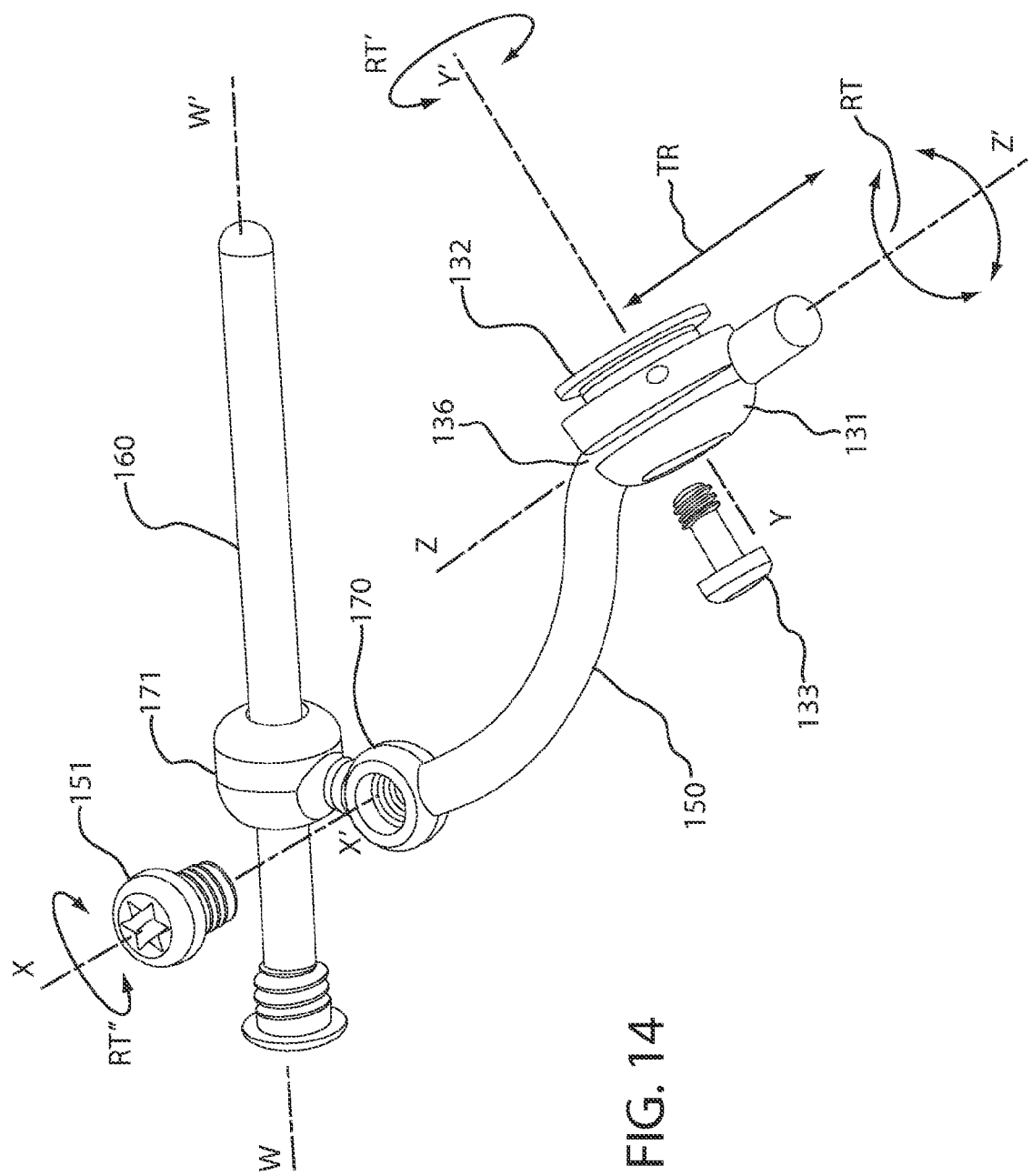
FIG. 14 is a partially exploded perspective view of selected portions of the internal joint stabilizer of FIG. 8.

As shown more particularly in FIGS. 14-15B, a swivel joint 170 can also be provided, permitting rotation of the neck portion 150 around the axis X-X' (RT'' of FIG. 14), while swivel joint screw 151 is loosely attached. More particularly, rotation of the swivel joint 170 allows the angular displacement of neck portion 150 relative to axis W-W' of axel portion 160 after such axle has been threadably attached to eyelet 171 of swivel joint 170. Rotation of swivel joint 170 can be impeded by fully tightening swivel joint screw 151.

Referring now to FIGS. 15A-15D, FIGS. 15A and 15B show exemplary translational displacements of neck portion 150 in the turret assembly 130. For example, FIG. 15A shows the neck portion 150 as fully inserted into the turret assembly 130 while FIG. 15B shows neck portion 150 fully extended above the turret assembly 130. FIGS. 15C-15D illustrate a further embodiment of swivel joint 170 where it can be observed that the corresponding surfaces of swivel joint 170 can be matchingly splined (i.e., "grooved") on the surfaces 173, 174 (as seen in FIG. 15C) or splined on one surface 173 and ridged circumferentially with a deformable (softer) metal on the other surface 175 (as seen in FIG. 15D) to advantageously allow the swivel joint to be fixed at any desired angle. In a still further embodiment it can be seen in FIG. 15D that neck portion 150' is totally straight, that is, totally aligned with axis Z-Z' as opposed to neck portion 150 (FIG. 15A-15B) that is partially straight and partially curved and where only the straight portion aligns with axis Z-Z'. Additionally, the lower end of neck portion 150, 150' can be grooved longitudinally with grooves 152 which provide increased friction with hole 135 and allow for burr-free cutting if, after installation, neck portion 150, 150' protrudes more than desired below turret portion 131.

Figure 16:
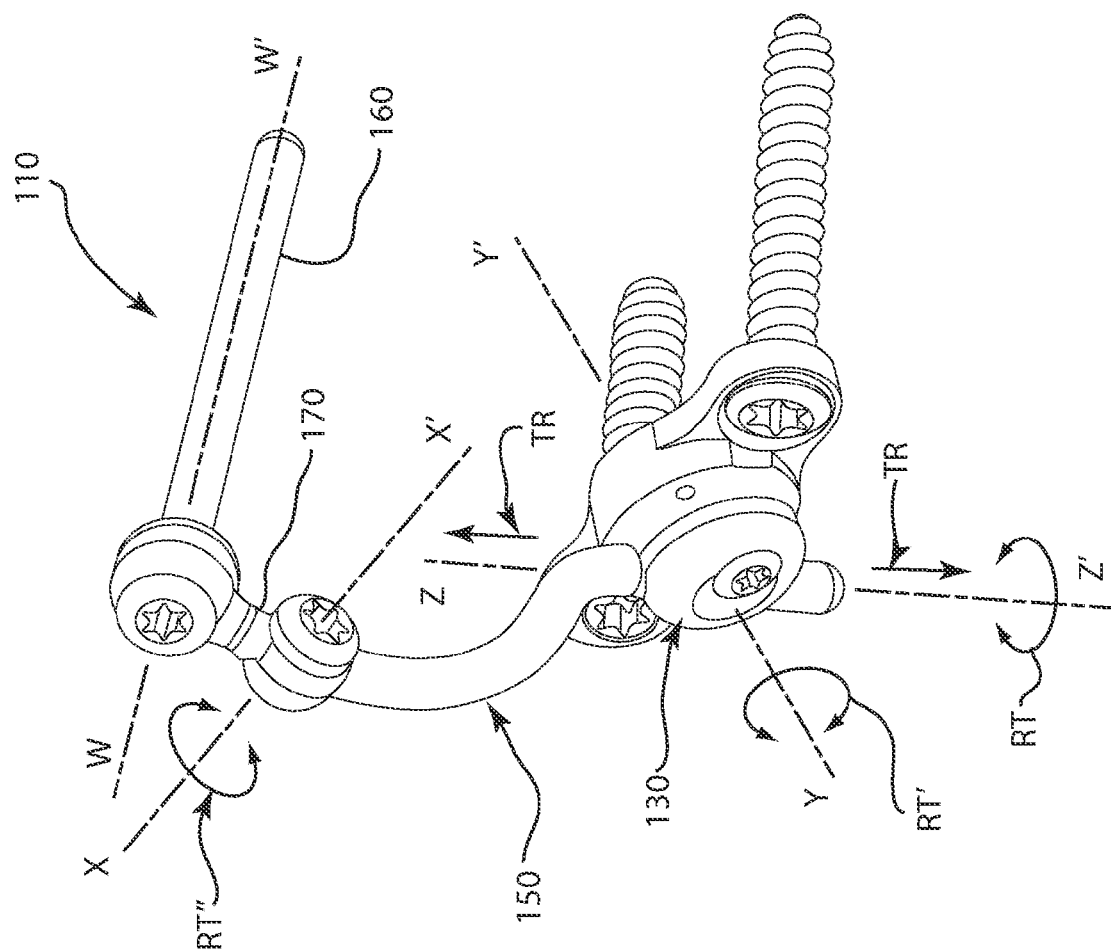
FIG. 16 is a perspective view of the internal joint stabilizer of FIG. 8 indicating the different types of adjustment capabilities.

Referring now to FIG. 16, the internal joint stabilizer 110 described in connection with FIGS. 8-15C, provides 4 degrees of freedom for adjustment: a.) rotation of neck portion 150, 150' around axis Z-Z' (RT); b.) longitudinal translation of neck portion 150, 150' along axis Z-Z' (TR); c.) rotation of turret assembly 130 around axis Y-Y' (RT') with resulting angular displacement of neck portion 150, 150'; and d.) angular displacement of neck portion 150, 150' relative to axle portion axis W-W' resulting from rotation of swivel joint 170 around axis X-X' (RT'').

Referring now to FIGS. 17A and 17B, there is shown a further embodiment of a plate portion and turret assembly for use with an internal joint stabilizer of the instant invention. For example, if desired, the plate 201 and turret assembly 200 of FIGS. 17A-17B can be substituted for the plate 120 and turret assembly 130 in the internal joint stabilizer 110 of FIGS. 8-16. More particularly, the plate 201 and turret assembly 200 are configured to provide the internal joint stabilizer of the instant invention with an additional degree of freedom for adjustment. As shown, turret assembly 200 includes a cylindrical hole 290, therethrough, which defines an axis V-V'. The cylindrical hole 290 receives a correspondingly sized cylindrical shaft portion 280, extending between the two plate sockets 295. Each plate socket 295 includes a screw hole 123 and can include protrusions 125, similar to those previously described in connection with the plate 120 of FIGS. 8-16. As also shown in FIG. 17B, the turret assembly 200 can be used with turret portion 131, turret nut portion 132 and turret set screw 133, of the previously described turret assembly 130. The turret assembly 200 can additionally mate with a neck portion 150, 150' in the manner described in connection with FIG. 14 above.

When plate portion 201 and turret assembly 200 are used as part of an internal joint stabilizer, such as the internal joint stabilizer 110 of FIG. 8, an additional (fifth) degree of freedom is advantageously obtained. More particularly, this further degree of freedom permits rotation of the turret assembly 200 around axis V-V' (RT'' of FIG. 17B), resulting in a further corresponding rotation of a connected neck portion 150, 150'.

Figure 18B:
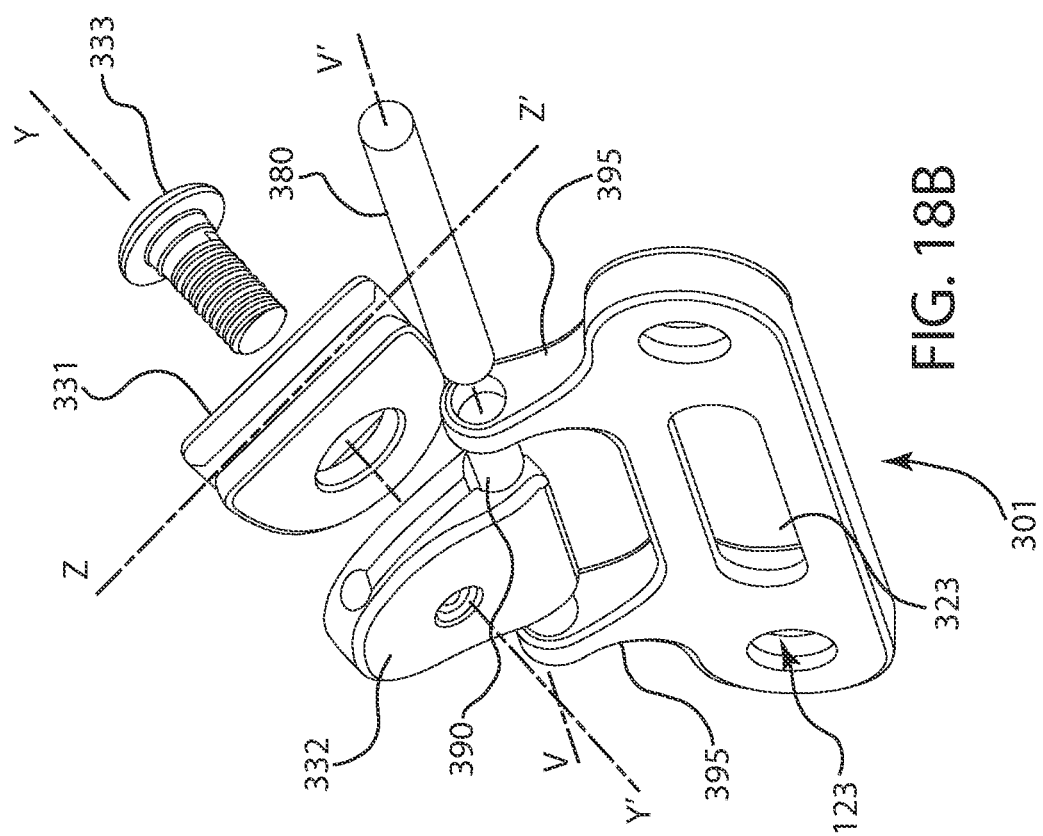
FIGS. 18A-18B are a perspective view and an exploded perspective view, respectively, of selected portions of an internal joint stabilizer in accordance with a further embodiment of the instant invention.
Figure 18A:
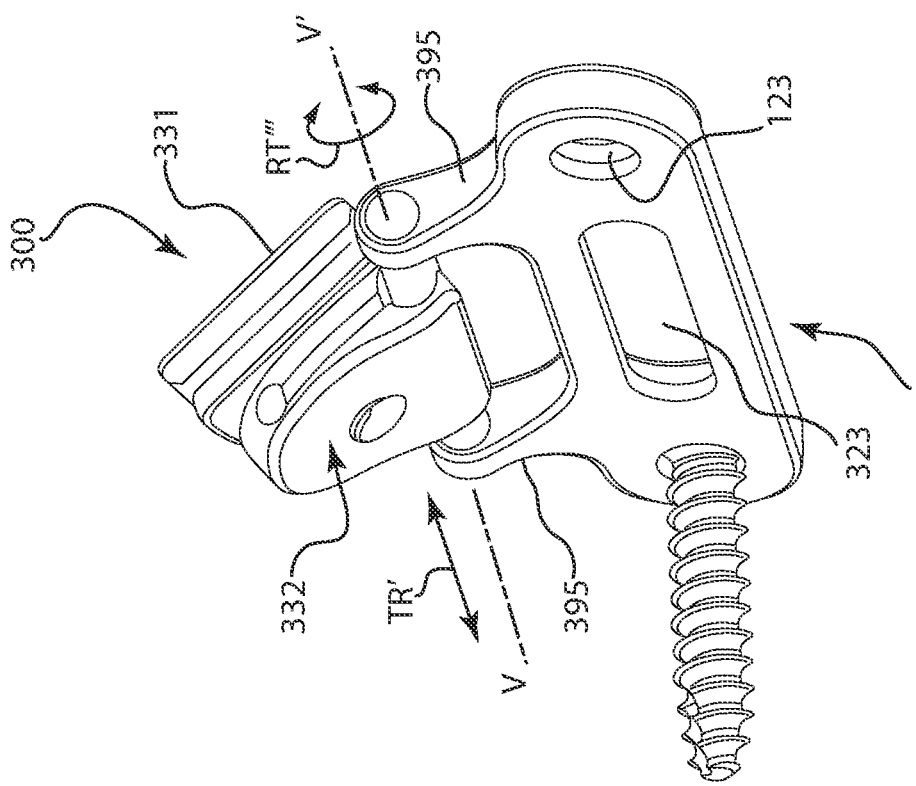

Referring now to FIGS. 18A and 18B, there is shown a further embodiment of a plate portion and turret assembly for use with an internal joint stabilizer of the instant invention. For example, if desired, the plate 301 and turret assembly 300 of FIGS. 18A-18B can be substituted for the plate 120 and turret assembly 130 in the internal joint stabilizer 110 of FIGS. 8-16. More particularly, the plate 301 and turret assembly 300 are configured to provide the internal joint stabilizer of the instant invention with one more additional degree of freedom for adjustment as that provided by the plate 201 and turret assembly 200. As shown, turret assembly 300 includes a cylindrical hole 390, therethrough, which defines an axis V-V'. The cylindrical hole 390 receives a cylindrical shaft portion 380 of corresponding diameter but of greater length than cylindrical hole 390, extending between the two plate extensions 395. Plate 301 includes a screw holes 123 similar to those previously described in connection with the plate 120 of FIGS. 8-16 and a slot 323 configured to receive a compression screw. As also shown in FIG. 18B, the turret assembly 300 includes turret portion 331, turret nut portion 332 and turret set screw 333, similar to previously described turret assembly 130. The turret assembly 300 can additionally mate with a neck portion 150, 150' along axis Z-Z' in the manner described in connection with FIG. 14 above.

When plate portion 301 and turret assembly 300 are used as part of an internal joint stabilizer, such as the internal joint stabilizer 110 of FIG. 8, an additional (sixth) degree of freedom is advantageously obtained. More particularly, this further degree of freedom permits longitudinal translation of the turret assembly 300 along axis V-V' (TR' of FIG. 18A), resulting in a further possible adjustment of a connected neck portion 150, 150'.

FIG. 18C shows internal joint stabilizer 310, which includes plate portion 301, turret assembly 300, neck portion 150', swivel joint 170 and axle portion 160 described above after installation on the posterior part of the ulna 21 in the humero-ulnar joint. It should be noted that the humerus 20 is shown semi-transparent to permit visualization of the axle portion 160 through the axis of rotation of the joint, while the ulna 21 and the radius 22 are shown solid.

To install an internal joint stabilizer of the instant invention, such as the internal joint stabilizer 110 of FIG. 8 or 310 of FIG. 18C, the surgeon approaches the elbow through a lateral or a medial incision. A first point on the axis of rotation is determined and marked. This can be accomplished by visual inspection of the anatomy. Alternatively, the joint can be moved through its range of motion allowing the surgeon to identify and mark the isometric point on the humerus which locates a first point on the axis of rotation. This point is located at the center of the capitulum, next to the base of the lateral epicondyle. Similarly, another end point of the axis of rotation on the opposite side of the humerus can be identified by fluoroscopy, direct inspection or with the aid of a guide (for example, the axis trajectory guide 400 of FIG. 19). A hole is then drilled connecting both end points of the axis of rotation in preparation for installation of the internal joint stabilizer.

All portions of the internal joint stabilizer 110, 310 with the exception of axle portion 160 are loosely assembled. While keeping the turret set screw (133, 333 of FIGS. 14, 18B) and the swivel joint screw (151 of FIG. 14) loosely attached in order to allow relative movement between its different portions, the surgeon introduces the internal joint stabilizer into the incision, while identifying an optimal location (lateral, medial or posterior) for installing the plate portion 120, 201, 301 to the ulna. The plate portion 120, 201, 301 is then attached to the ulna with compression screws or with angle-stable screws, as desired. The eyelet of the swivel joint (171 of FIG. 14) is moved into contact with the humerus just opposite the entry point of the hole previously drilled in the humerus. An appropriately sized axle portion 160 is inserted through the eyelet 171 and into the previously drilled hole. Axle portion 160 is tightly screwed into the eyelet 171. The surgeon adjusts the longitudinal and angular position of the neck portion 150, 150' by rotating and sliding along axis Z-Z' and by rotating the turret portion (131 of FIG. 14 and FIG. 17B or 331 of FIGS. 18A-18B) and by adjusting the rotation of the swivel joint (170 of FIG. 14). The swivel joint screw (151 of FIG. 14) and the turret set screw (133 of FIG. 14 and FIG. 17B or 333 of FIG. 18B) are tightened and range of motion is tested. If necessary finer adjustments are performed by sequentially loosening and tightening the turret set screw 133, 333 and/or the swivel joint screw 151 until optimal range of motion is achieved. Incisions are then closed by the surgeon in standard fashion.

Referring now to FIGS. 19-27, therein will be described an axis trajectory guide and method that can, optionally, be used to locate the axis of rotation of a joint, prior to stabilization using one of the devices described in connection with FIGS. 1-18C. It is important to note that the axis trajectory guide can be used as part of a system, in combination with the internal joint stabilizer devices described herein, but is not limited thereto. Rather, the axis trajectory guide of FIGS. 19-27 can also be used to locate the axis of rotation of a joint for the insertion of a known and/or different type of fixator or joint stabilizer or in any other situation when it is desired to locate the axis of rotation of a joint.

In order to locate the axis of rotation of a joint, it is sufficient to identify two points pertinent to the joint's rotation. Once identified, the axis of rotation for the joint can be represented by a straight line containing the two identified points.

For example, referring to the case of an elbow joint for illustrative purposes only, the location of two pertinent points of rotation of this joint will permit the axis of rotation to be visualized. Approaching the humero-ulnar joint through a lateral incision a surgeon can visually identify one such point. This first point is located in the center of the capitulum next to the base of the lateral epicondyle. A second point can be assumed to be a point in the center line of the "spool" shaped trochlea (the humeral portion of the ulnar-humeral joint). In order to locate this point, a guide is provided herein, such as the axis trajectory guide 400 of FIG. 19, having an arcuate (i.e. in the shape of an arc of a circle) portion that can be fitted over the trochlea to particularly identify a second point on the axis.

Figure 19:
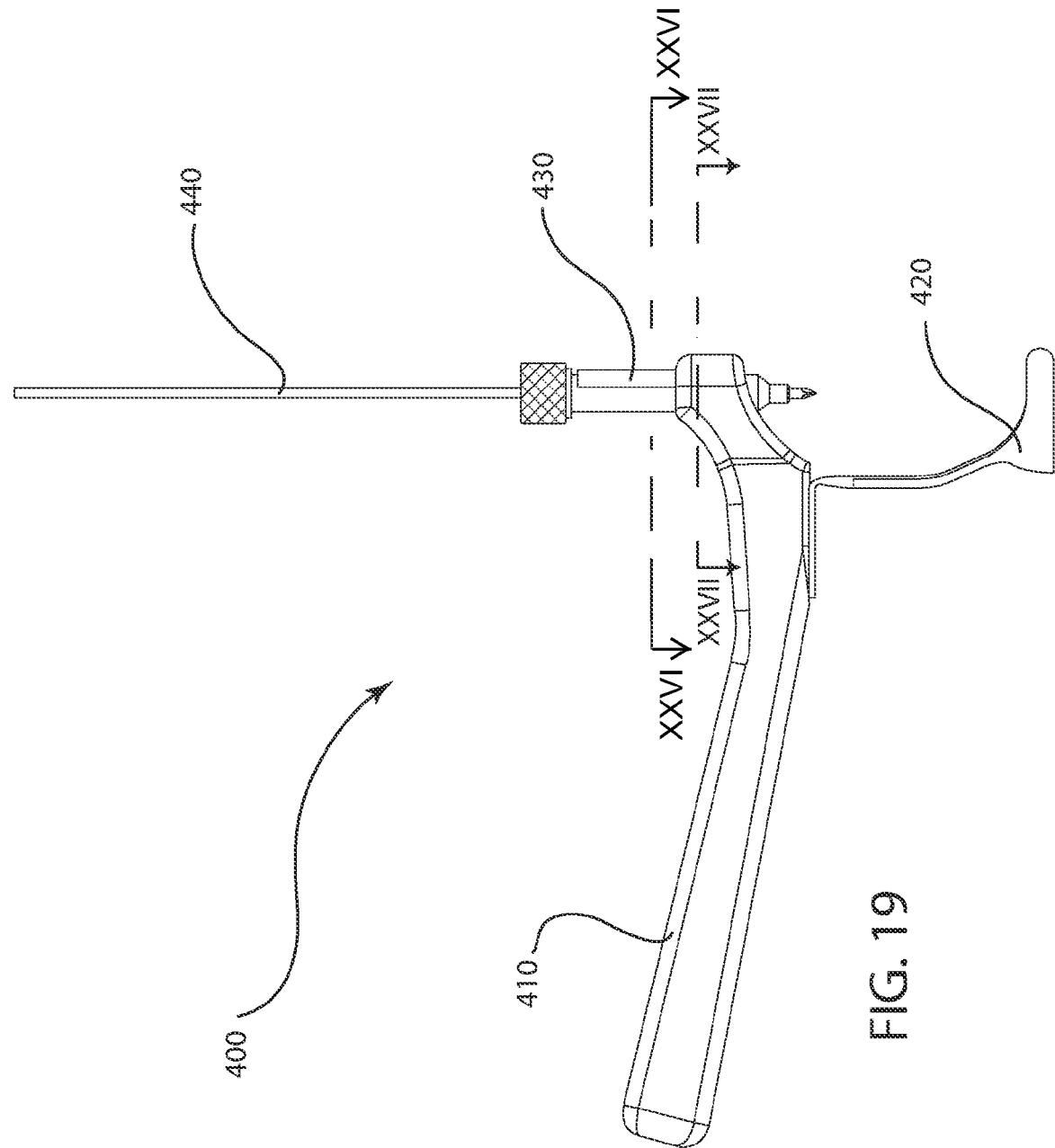
FIG. 19 is a side elevational view of an axis trajectory guide and its component parts, in accordance with one particular embodiment of the present invention
Figure 20:
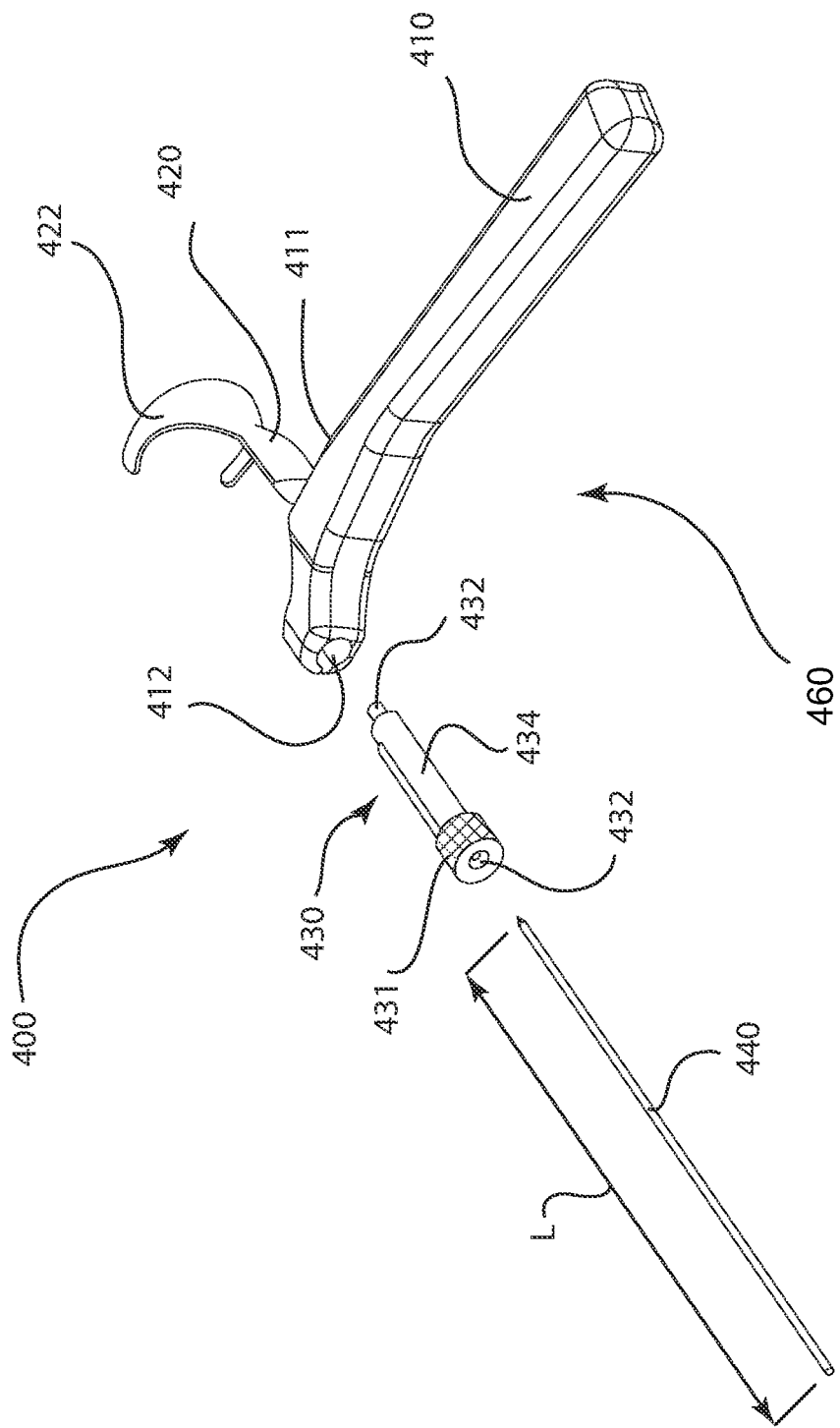
FIG. 20 is an exploded view of the axis trajectory guide of FIG. 19.

The axis trajectory guide 400 of FIG. 19 will now be described, more particularly, in connection with FIGS. 19-20. Referring now to FIG. 19, there is shown an elevational view of an axis trajectory guide and its principal component parts, in accordance with one particular embodiment of the present invention. FIG. 20 is a perspective exploded view of the axis trajectory guide 400 of FIG. 19.

In particular, the axis trajectory guide 400 of FIGS. 19-20 includes a handle portion 410, a center locator 420, and a removable alignment sleeve 430 which is configured to receive a K-wire 440 of known length L. The handle portion 410 can be made from any desired material, but is preferably made of metal, such as stainless steel, or plastic.

As shown more particularly in FIG. 20, the center locator 420 of the axis trajectory guide 400 includes an arcuate distal portion 422 defining a periphery. Please note that the arcuate distal portion of the center locator need not be limited to proscribing a particular arc of a circle. Rather, if desired, the partially open arcuate area defined can be equal to a semi-circle, larger than a semi-circle as shown in FIG. 20, or even smaller, as desired. Center locators 420 with different diameters of distal portion 422 can be provided to accommodate different anatomies. The proximal end of the center locator 420 can be either fixed to (as shown), integrally formed with or, preferably, removably attached to, a distal end 411 of the handle portion 410, thus, together, forming the body of the axis trajectory guide 400. Additionally, handle portion 410 is configured to receive the cannulated extension pin portion 434 of removable alignment sleeve 430 through opening 412 located on the side of handle portion 410 which is opposite to the location of center locator 420. Note that, when adapted for use in joints other than the elbow, the distal portion of the center locator 420 of the axis trajectory guide 400 would be, correspondingly, geometrically adapted to engage a portion of a bone in the joint and locate the desired axis trajectory thereof.

The removable alignment sleeve 430 further includes a knob 431 having an opening 432 therethrough that further continues through cannulated extension pin 434. The opening 432 is sized to receive a K-wire 440 of known length L or other type of longitudinally extending device, as shown more particularly in FIG. 20. As seen more clearly in FIGS. 26-27 the cross-section of cannulated extension pin 434 is cylindrical throughout approximately three quarters (¾) of its perimeter, the last quarter protruding slightly to form a cam. When the cam is in neutral position as shown on FIGS. 26-27 the cannulated extension pin 434 can slide longitudinally along the axis of opening 412. By rotating knob 431 clockwise the cam shaped cannulated extension pin 434 engages the correspondingly configured opening 412, locking it in place and thereby impeding further longitudinal sliding of cannulated extension pin 434 along the axis of opening 412.

The center locator 420, alignment sleeve 430 and K-wire 440 can be made of any desired material, but, preferably, are made of metal, such as stainless steel.

A method for using the axis trajectory guide 400 of FIG. 19 will now be described in connection with FIGS. 21-27 using an elbow joint, for illustrative purposes. The surgeon proceeds, as previously described, by approaching the humero-ulnar joint through a lateral incision and marking a first point 460 (as seen in FIG. 21) on the axis of rotation of the joint.

Figure 21:
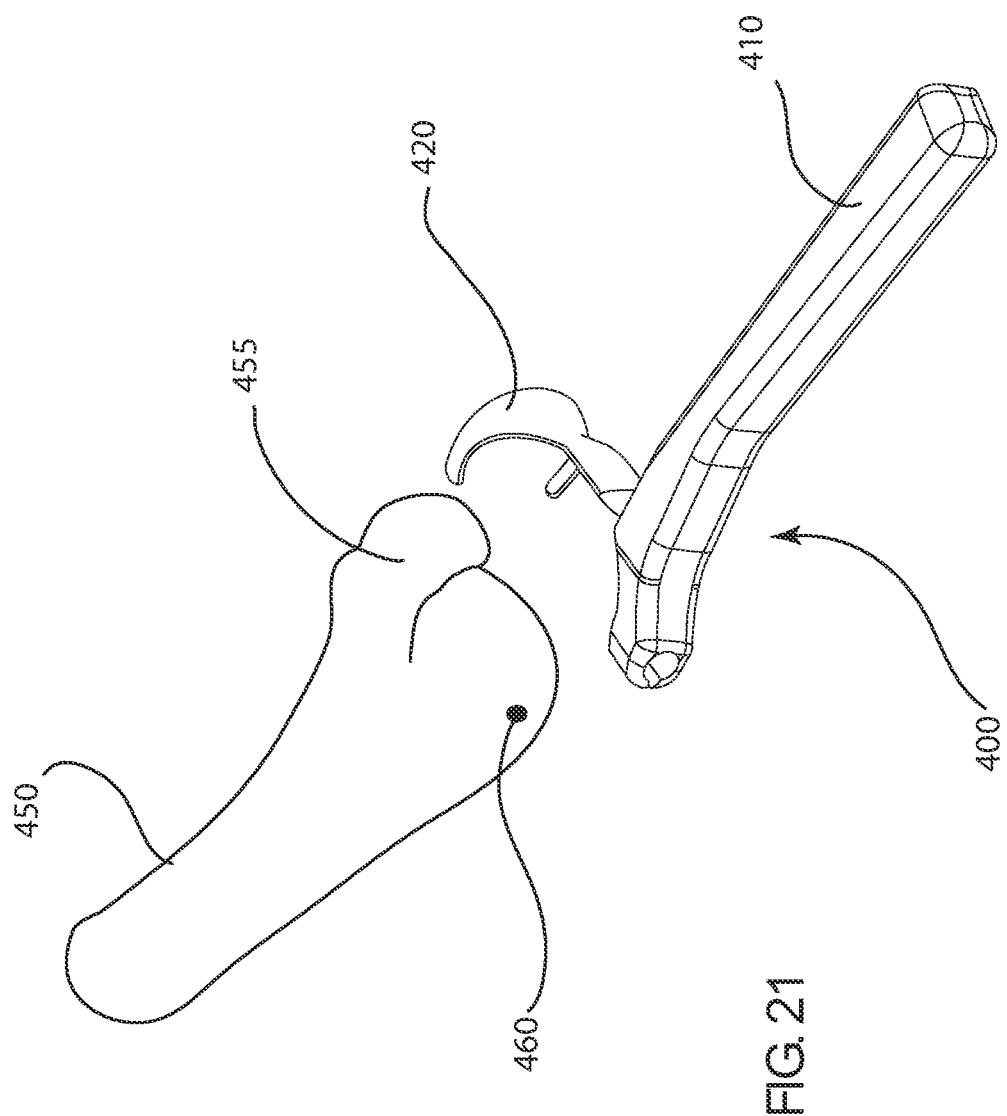

Referring now to FIG. 21, the surgeon distracts the humerus from the ulna and inserts the center locator 420 into the distracted joint until it "sits" on the humeral trochlea 455. The handle 410 is used to manipulate the center locator 420 into the joint.

Figure 22:
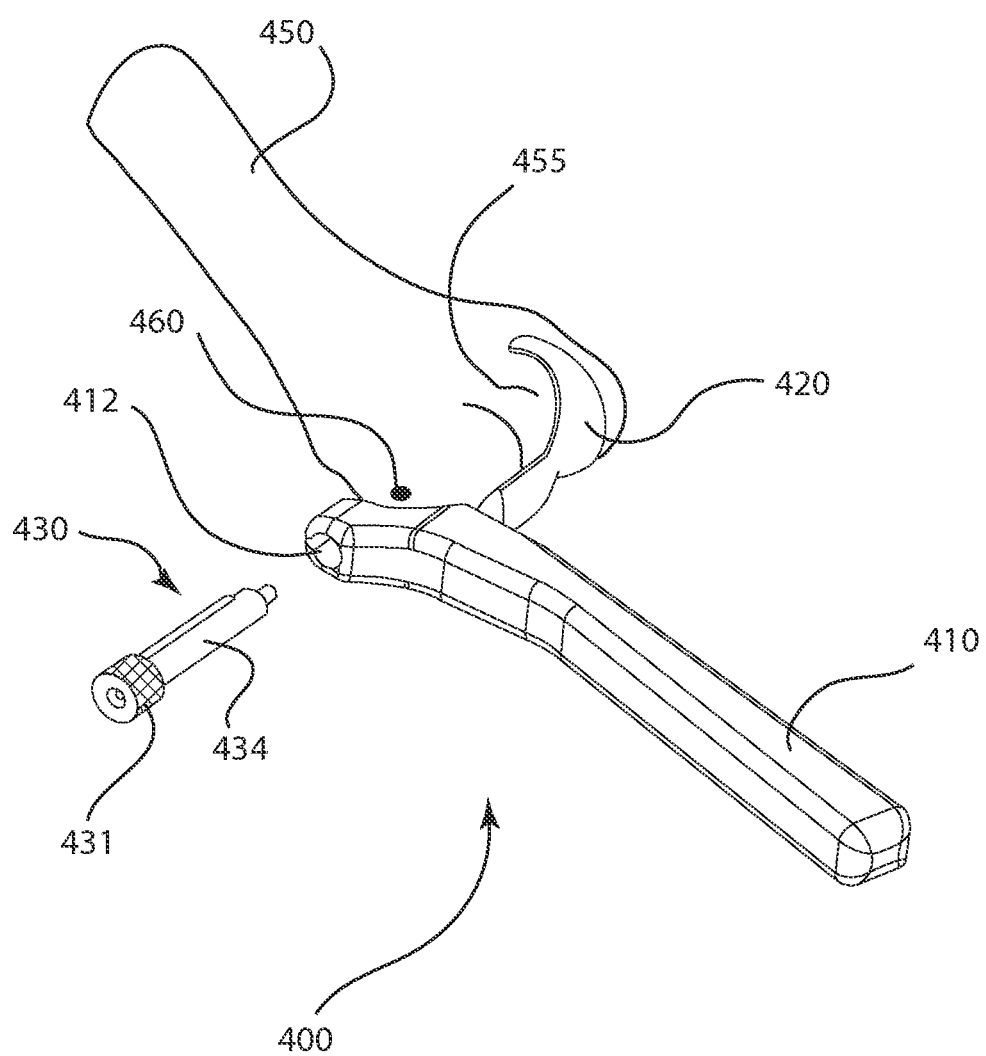
Figure 23:
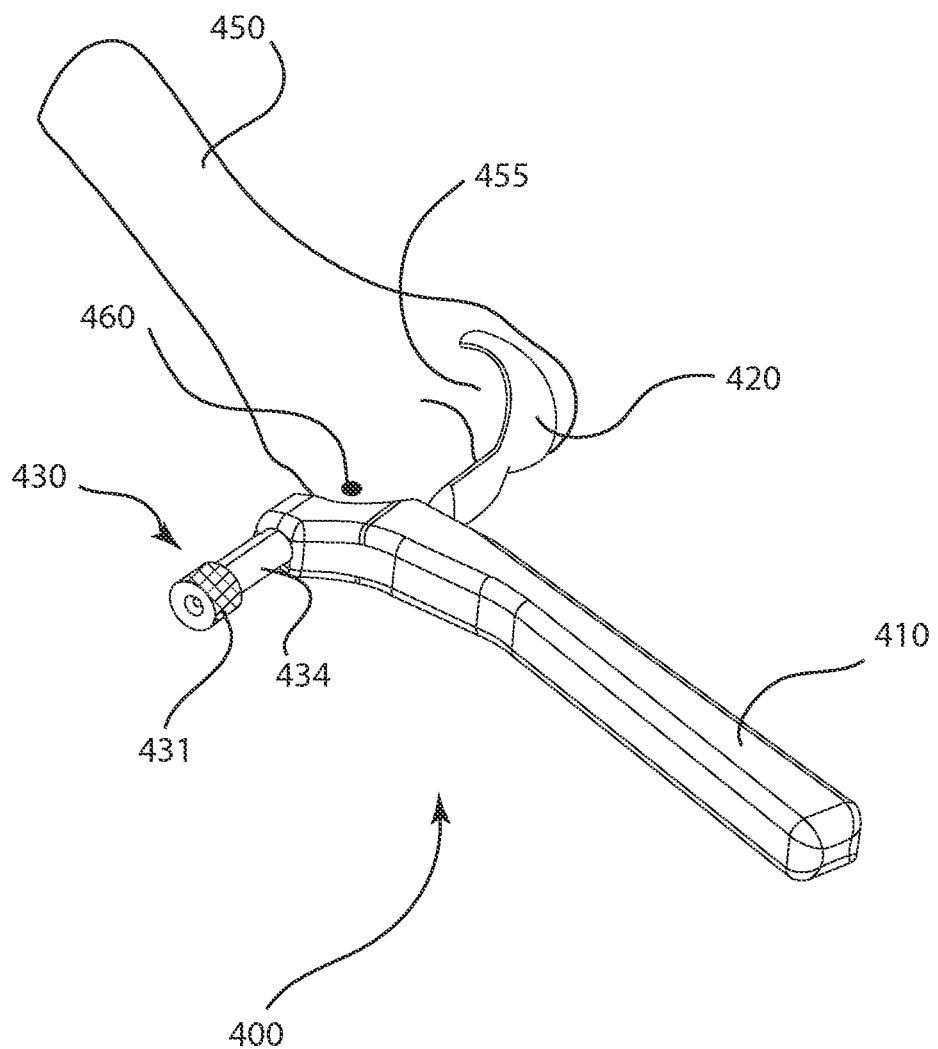

As shown in FIGS. 22-23, once the center locator 420 has been correctly seated on the trochlea 455, the cannulated extension pin 434 of the alignment sleeve 430 is inserted into the opening 412 in the handle portion 410 of the axis trajectory guide 400 so that the distal end of cannulated extension pin 434 is almost touching the first point 460 previously marked by the surgeon on the humerus 450 but sufficiently distant to allow visual observation of point 460. The surgeon then locks the cannulated extension pin 434 in that position by turning knob 431 clockwise.

Figure 24:
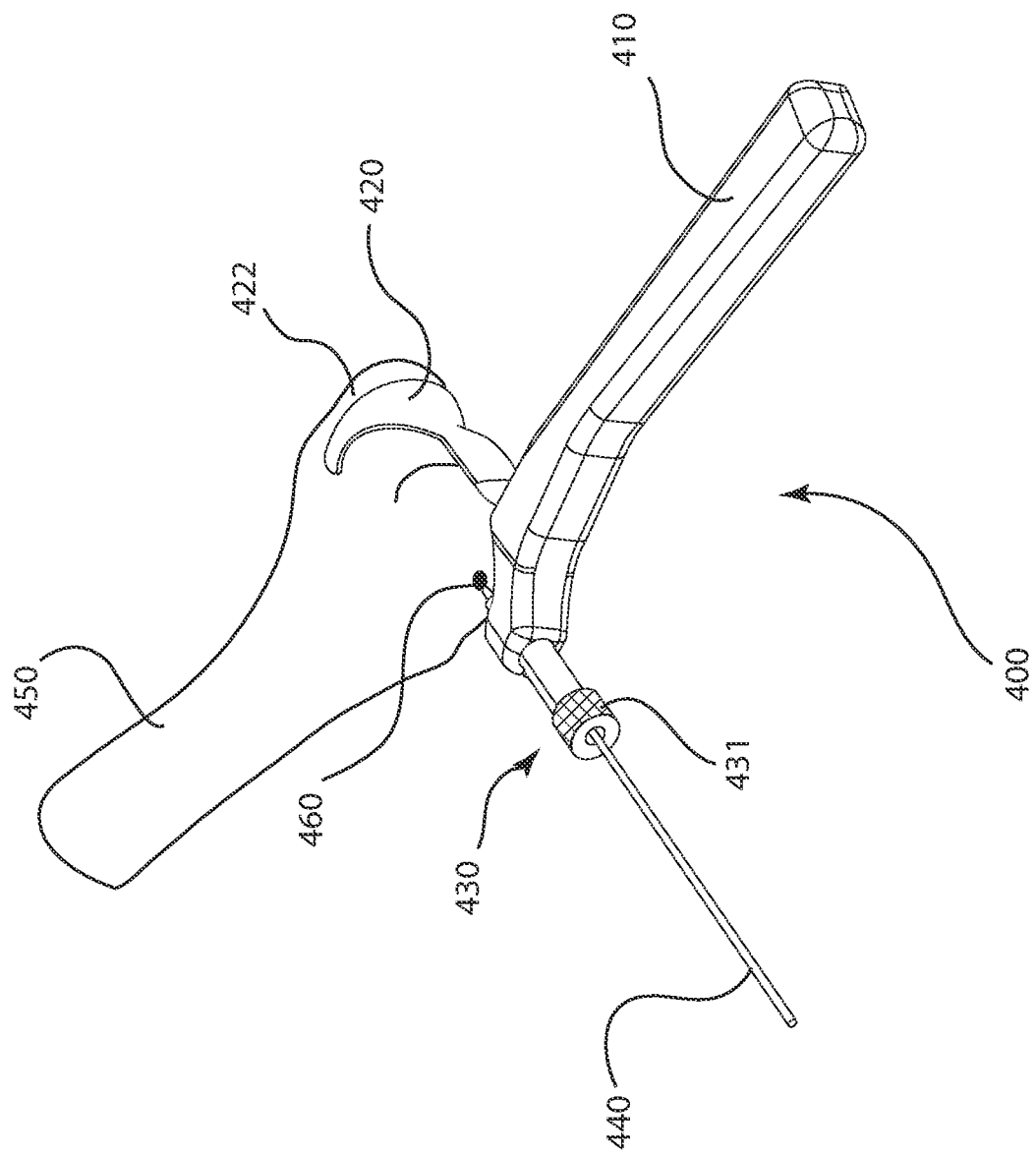

As further shown in FIG. 24, once the alignment sleeve 430 has been locked within opening 412 of handle portion 410, the surgeon inserts a K-wire 440 of known length L until it engages the humerus 450 at first marked point 460.

Under fluoroscopy, the K-wire 440 is carefully drilled into the humerus 450, while the surgeon visually ascertains that the K-wire 440 is centered within the arcuate portion 422 of the center locator 420 and while taking care to drill to just beyond the distal edge of the arcuate portion 422 of the center locator 420 but short of the distal cortex of the humerus.

Figure 25:
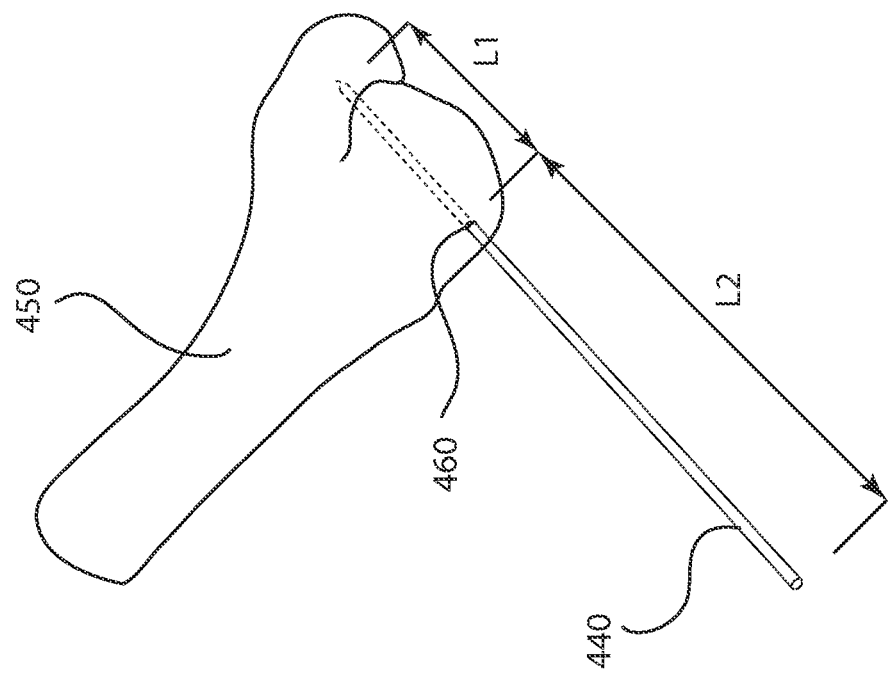
Figure 26:
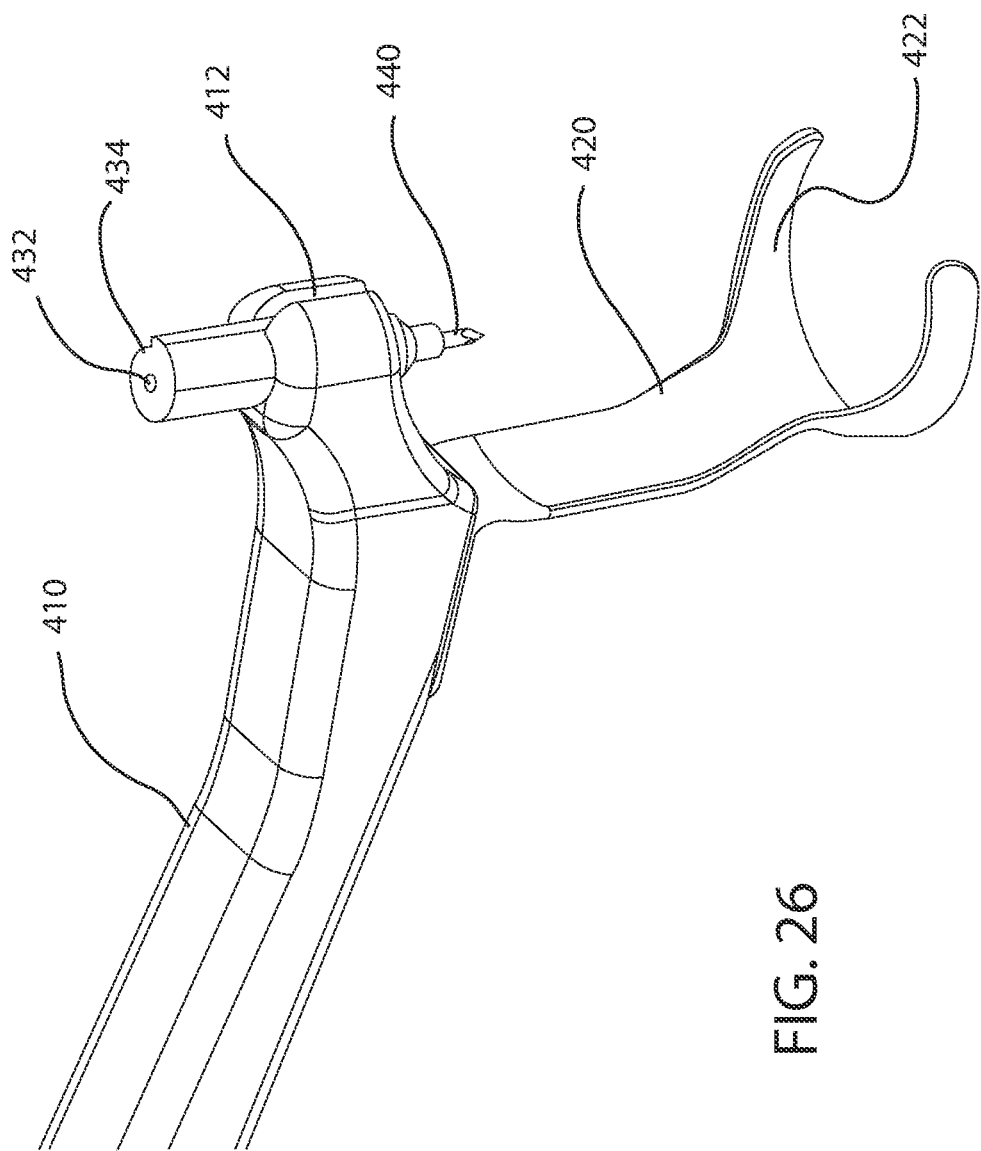

Referring now to FIGS. 24-25, subsequent to the placement of the K-wire 440, the knob 431 on alignment sleeve 430 is turned counterclockwise to release the cannulated alignment pin 434. The alignment sleeve 430 is first removed from opening 412 and then the remainder of axis trajectory guide 400 is removed from the joint, while the K-wire 440 is left in place. The K-wire 440 now defines the axis of rotation of the joint. Using a depth gauge (not shown) the surgeon measures the protruding length L2 of K-wire 440. Since the total length L of K-wire 440 is known, the length L1 of K-wire 440 embedded in humerus 450 is calculated and noted.

Thus defined, the axis of rotation of the subject joint, as located using the axis trajectory guide 400 of FIGS. 18-26, can be used to further act on the subject joint. For example, the surgeon can use a cannulated drill to insert over the K-wire 440 and create a cylindrical cavity of now known length L1 aligned to the natural axis of rotation of the joint and capable of accepting an axle portion 160 of, at most, length L1 of a joint stabilizing device.

The axis trajectory guide and method described herein can be used to locate the axis of rotation of a joint in order to facilitate the stabilization of that joint utilizing an internal and/or external joint stabilizer. However, as noted above, this is not meant to be limiting, as the presently described guide and method can be used in any situation wherein it is desired to locate the axis of a joint, whether or not the joint is subsequently stabilized.

It is advantageous to provide the axis trajectory guide described herein as part of a kit including the internal joint stabilizer device, wherein the kit can also include a plurality of axles and necks of different lengths, to permit the surgeon to adapt an internal joint stabilizer to the anatomy of the particular patient, intraoperatively. For example, after determining the length L1, the surgeon can select an axle having a body length shorter than, but closely approximating, the length L1 from a plurality of axles provided in the kit. Similarly, the surgeon can select a neck portion, intraoperatively, from a plurality of necks of different lengths and shapes provided in the kit, order to accommodate the particular anatomy of the patient. In such an embodiment, the selected neck can be further attached to one of a plurality of adjustment portions, such as the different turret assemblies described herein.

Although described above in connection with the elbow and the interphalangeal joints, this is not meant to be limiting, as other internal joint stabilizers and axis trajectory guides can be made in accordance with the description herein, but of different size or scale, so as to treat instability, subluxation or dislocation of other joints, such as the ankle, or chronic instability such as occurs on the first metatarso-phalangeal joint or bunion. Additionally, it can be seen from the description herein that the internal joint stabilizer of the present invention can be adapted for use with joints having more complex translational geometries, or more than one axis of rotation, such as the carpometacarpal (CMC) joint of the thumb or the knee, wherein the device would be adapted to allow for the unique motions of these joints. For example, in one particular embodiment, the internal joint stabilizer of the present invention can be modified to further include more than one axle or linkage arms placed at the appropriate isometric points. As such, although the invention is illustrated and described herein in various embodiments including an axle portion that is rotatable relative to a fixable portion using various particularly described mechanisms, such as a bendable neck portion, a turret assembly and/or a swivel portion, etc., it is nevertheless not intended to be limited to only these details shown, since various modifications and structural changes may be made therein without departing from the spirit of the invention and within the scope and range of equivalents of the claims.

We claim:

1. An internal joint stabilizer for stabilizing a joint between a first bone and a second bone, the joint having a natural axis of rotation, the internal joint stabilizer comprising:
    an axle configured for insertion into the first bone of the joint in alignment with the natural axis of rotation of the joint;
    said axle further configured to allow free rotation of the first bone of the joint around said axle;
    an attaching portion to be attached to the second bone with fasteners; and
    a neck disposed between said axle and said attaching portion, wherein the position of said axle is movable relative to said neck.

2. The internal joint stabilizer of claim 1, wherein the internal joint stabilizer further comprises a prosthetic device affixed to said first bone, said prosthetic device including a hole for receiving said axle.

3. The internal joint stabilizer of claim 1, wherein at least one of said axle and said neck are formed from a pin or wire.

4. The internal joint stabilizer of claim 3, wherein the attaching portion is additionally formed from the same piece of pin or wire as said axle and said neck.

5. The internal joint stabilizer of claim 4, wherein the internal joint stabilizer comes pre-formed from the factory.

6. The internal joint stabilizer of claim 1, wherein at least a portion of the internal joint stabilizer is bio-absorbable.

7. The internal joint stabilizer of claim 1, wherein said attaching portion includes a plate.

8. The internal joint stabilizer of claim 1, wherein at least one of said neck and said attaching portion are bendable by hand during a surgical procedure.

9. The internal joint stabilizer of claim 1, wherein said neck and said axle are connected by a lockable swivel joint.

10. The internal joint stabilizer of claim 1, wherein the position of said neck is movable relative to said attaching portion.

11. The internal joint stabilizer of claim 10, wherein said attaching portion includes a plate including a mounting portion and said neck is attached to said mounting portion.

12. The internal joint stabilizer of claim 11, wherein said neck is rotatable in said mounting portion and linearly displaceable relative to said mounting portion.

13. The internal joint stabilizer of claim 11, wherein said mounting portion includes a fixation element such that said mounting portion is rotatable relative to the plate when said fixation element is in a first position and the movement of said mounting portion is fixed relative to the plate when said fixation element is in a second position.

14. The internal joint stabilizer of claim 13, wherein said fixation element includes a set screw and said first position is a loosened position and said second position is a fully tightened positioned of said set screw.

15. The internal joint stabilizer of claim 13, wherein said fixation element additionally impedes the movement of said neck relative to said mounting portion when said fixation element is in said second position.

16. The internal joint stabilizer of claim 11 wherein said mounting portion includes a turret means for mounting the neck relative to the plate.

17. The internal joint stabilizer of claim 16, wherein said turret means includes a turret portion rotationally movable relative to the plate.

18. The internal joint stabilizer of claim 16, wherein said plate includes a bar and said turret means is pivotally mounted around said bar.

19. The internal joint stabilizer of claim 18, wherein said turret means is additionally displaceable along said bar.

20. The internal joint stabilizer of claim 18, wherein said turret means includes a portion that additionally rotates about an axis perpendicular to an axis extending through the length of said bar.

21. The internal joint stabilizer of claim 1, wherein the internal joint stabilizer is part of a kit including at least one of a plurality of necks of different shapes and/or different lengths and at least one of a plurality of axles of different diameters and/or different lengths from which to select one axle and one neck to configure the internal joint stabilizer.

22. An internal joint stabilizer for stabilizing a joint between a first bone and a second bone, the joint having a natural axis of rotation, the internal joint stabilizer comprising:
    an axle configured for insertion into the first bone of the joint in alignment with the natural axis of rotation of the joint;
    said axle further configured to allow free rotation of the first bone of the joint around said axle;
    a plate attachable to the second bone with fasteners, said plate including a bar and a mounting portion, said mounting portion being pivotally mounted around said bar; and
    a neck disposed between said axle and said mounting portion.

23. The internal joint stabilizer of claim 22, wherein at least one of said axle and said neck is movable relative to said plate.

24. The internal joint stabilizer of claim 23, wherein said neck includes a lockable swivel joint for moving said axle relative to said plate.

25. The internal joint stabilizer of claim 23, wherein said mounting portion is additionally slideable along said bar.

26. The internal joint stabilizer of claim 23 wherein a turret on said mounting portion is rotatable relative to a base of said mounting portion, said neck being attached to said turret and said base being pivotally mounted around said bar.

27. The internal joint stabilizer of claim 26, wherein said neck is additionally displaceable longitudinally relative to said turret.

28. A method for performing stabilization of a joint between a first bone and a second bone, the joint having a natural axis of rotation, comprising the steps of:

providing an internal device according to claim 1;

locating the axis of rotation of the joint;

inserting the axle into a first bone forming the joint, in alignment with the axis of rotation of the joint; and attaching the attaching portion to a second bone of the joint.

29. The method of claim 28, wherein the method further includes the step of replacing a portion of the first bone with a prosthetic device prior to inserting the axle.

30. The method of claim 28, wherein the internal device additionally includes a movable portion permitting movement of the axle relative to the fixable portion.

31. The method of claim 30, wherein the movable portion includes a turret means.

32. The method of claim 30, further comprising the step of moving the movable portion prior to fixing the fixable portion to the second bone.

33. The method of claim 28, wherein a guide device is used in the locating step.

34. The method of claim 33, wherein the locating step includes the steps of:

identifying and marking a first point of rotation of the joint;

utilizing the guide device to identify the second point on the axis.

35. The method of claim 34 wherein the identifying step includes the step of visually identifying the first point.

36. A system for stabilizing a joint, comprising:

an internal joint stabilizer kit, including:

an internal joint stabilizer according to claim 1; and a guide for locating the natural axis of rotation of the joint, said guide, including a handle portion;

a center locator attached to the handle portion, said center locator forming a periphery; and an alignment sleeve having a bore defined therethrough, such that an axis through said bore additionally extends through the interior of said periphery.

37. The system of claim 36, wherein the kit includes at least one of a plurality of necks of different shapes and/or different lengths and a plurality of axles of different diameters and/or different lengths from which to select the axle and neck of the internal joint stabilizer.

38. A method for fixing a joint using the system of claim 37, the method comprising:

locating an axis of rotation of a joint, by:

identifying and marking a first point of rotation of the joint;

with the handle, manipulating the center locator of the guide into a distracted joint until the center locator sits on a predetermined portion of a first bone in the joint;

after the center locator is seated, aligning the alignment sleeve with the marked first point; and inserting a wire into said alignment sleeve and drilling the wire partially through the bone; and removing the guide and wire to expose a hole through the bone in alignment with the axis of rotation of the joint;

selecting at least one of the plurality of necks and axles for use as the neck or axle of the internal joint stabilizer;

connecting the axle to the attaching portion using the neck;

inserting the axle of the internal joint stabilizer into the hole; and fixing the attaching portion to a second bone of the joint.

39. The method of claim 38, wherein after removing the guide but before removing the wire the removing step additionally includes the step of drilling over the wire to enlarge the hole in the bone in alignment with the axis of rotation of the joint.

40. The system of claim 36, wherein the periphery of the center locator is an arc of a circle.

41. The system of claim 36, wherein the neck is connected to the attaching portion by a turret means.

42. A method for fixing a joint using the system of claim 36, the method comprising:

locating an axis of rotation of a joint, by:

identifying and marking a first point of rotation of the joint;

with the handle, manipulating the center locator of the guide into a distracted joint until the center locator sits on a predetermined portion of a first bone in the joint;

after the center locator is seated, aligning the alignment sleeve with the marked first point; and inserting a wire into said alignment sleeve and drilling the wire partially through the bone; and removing the guide and wire to expose a hole through the bone in alignment with the axis of rotation of the joint;

inserting the axle of the internal joint stabilizer into the hole; and fixing the attaching portion to a second bone of the joint.

43. The method of claim 42, wherein after removing the guide but before removing the wire the removing step additionally includes the step of drilling over the wire to enlarge the hole in the bone in alignment with the axis of rotation of the joint.

* * * * *